(12) United States Patent
Fallin et al.

(10) Patent No.: US 10,143,462 B2
(45) Date of Patent: Dec. 4, 2018

(54) TRANSOSSEOUS SUTURE ANCHOR METHOD

(71) Applicant: KATOR, LLC, Logan, UT (US)

(72) Inventors: T. Wade Fallin, Hyde Park, UT (US); Joel Helgerson, Erie, CO (US)

(73) Assignee: KATOR, LLC, Logan, UT (US)

( * ) Notice: Subject to any disclaimer, the term of this patent is extended or adjusted under 35 U.S.C. 154(b) by 188 days.

(21) Appl. No.: 15/224,284

(22) Filed: Jul. 29, 2016

(65) Prior Publication Data

US 2017/0035552 A1 Feb. 9, 2017

Related U.S. Application Data

(60) Provisional application No. 62/200,696, filed on Aug. 4, 2015.

(51) Int. Cl.
*A61B 17/04* (2006.01)
*A61F 2/08* (2006.01)
(Continued)

(52) U.S. Cl.
CPC .... *A61B 17/0401* (2013.01); *A61B 17/06133* (2013.01); *A61F 2/0811* (2013.01); *A61B 17/0485* (2013.01); *A61B 90/92* (2016.02); *A61B 2017/0053* (2013.01); *A61B 2017/0403* (2013.01); *A61B 2017/045* (2013.01);
(Continued)

(58) Field of Classification Search
CPC ........... A61B 17/0401; A61B 17/06133; A61F 2/0811
See application file for complete search history.

(56) References Cited

U.S. PATENT DOCUMENTS 1,583,271 A   5/1926   Biro
1,586,721 A   5/1932   Nagelmann
(Continued)

FOREIGN PATENT DOCUMENTS

WO   WO1998006344 A1   2/1998
WO   WO2003065904 A1   8/2003
(Continued)

OTHER PUBLICATIONS

Comprehensive Product Offerings for your Rotator Cuff Repair, Smith & Nephew, Inc., www.smith-nephew.com, 2015, 12 pp.
(Continued)

*Primary Examiner* — Tuan V Nguyen
(74) *Attorney, Agent, or Firm* — David Meibos; Maywood IP Law

(57) ABSTRACT

Methods are disclosed for attaching a suture to a bone. One exemplary method includes passing a portion of a suture through a bone so that a first portion of the suture extends from a first opening in the bone and a second portion of the suture extends from a second opening in the bone, passing the second portion of the suture through a portion of a suture anchor body in a proximal to distal direction, the suture anchor body having a proximal end and a distal end, passing the second portion of the suture alongside an outer surface of the suture anchor body in a distal to proximal direction, and then inserting the suture anchor into the bone through one of the first and second openings, the distal end being inserted first through the opening.

19 Claims, 23 Drawing Sheets

(51) Int. Cl.
- *A61B 17/06* (2006.01)
- *A61B 17/00* (2006.01)
- *A61B 90/00* (2016.01)
- *A61B 90/92* (2016.01)

(52) U.S. Cl.
CPC .............. *A61B 2017/0409* (2013.01); *A61B 2017/0412* (2013.01); *A61B 2017/0414* (2013.01); *A61B 2017/0424* (2013.01); *A61B 2017/0425* (2013.01); *A61B 2017/0458* (2013.01); *A61B 2090/037* (2016.02); *A61B 2090/0807* (2016.02); *A61F 2002/0835* (2013.01); *A61F 2002/0882* (2013.01)

(56) References Cited

U.S. PATENT DOCUMENTS

| | | |
|---|---|---|
| 4,441,497 A | 4/1984 | Paudler |
| 4,622,960 A | 11/1986 | Tam |
| 4,672,957 A | 6/1987 | Hourahane |
| 4,738,255 A | 4/1988 | Goble |
| 4,741,330 A | 5/1988 | Hayhurst |
| 4,784,126 A | 11/1988 | Hourahane |
| 4,809,408 A | 3/1989 | Abrahamson |
| 4,890,615 A | 1/1990 | Caspari |
| 4,898,156 A | 2/1990 | Gatturna |
| 4,959,069 A | 9/1990 | Brennan |
| 5,037,422 A | 8/1991 | Hayhurst |
| 5,041,129 A | 8/1991 | Hayhurst |
| 5,100,417 A | 3/1992 | Cerier |
| 5,176,682 A | 1/1993 | Chow |
| 5,224,946 A | 7/1993 | Hayhurst |
| 5,236,445 A | 8/1993 | Hayhurst |
| 5,250,055 A | 10/1993 | Moore |
| 5,254,126 A | 10/1993 | Filipi |
| 5,258,016 A | 11/1993 | DiPoto |
| 5,268,001 A | 12/1993 | Nicholson |
| 5,269,809 A | 12/1993 | Hayhurst |
| 5,312,438 A | 5/1994 | Johnson |
| 5,336,240 A | 8/1994 | Metzler |
| 5,342,369 A | 8/1994 | Harryman, II |
| 5,350,380 A | 9/1994 | Goble |
| 5,354,300 A | 10/1994 | Goble |
| 5,411,523 A | 5/1995 | Goble |
| 5,417,691 A | 5/1995 | Hayhurst |
| 5,417,701 A | 5/1995 | Holmes |
| 5,439,467 A | 8/1995 | Benderev |
| 5,454,823 A | 10/1995 | Richardson |
| 5,464,427 A | 11/1995 | Curtis |
| 5,466,243 A | 11/1995 | Schmieding |
| 5,480,403 A | 1/1996 | Lee |
| 5,486,197 A | 1/1996 | Le |
| 5,544,664 A | 8/1996 | Benderev |
| 5,545,180 A | 8/1996 | Le |
| 5,562,683 A | 10/1996 | Chan |
| 5,562,684 A * | 10/1996 | Kammerer ......... A61B 17/0401 289/17 |
| 5,562,687 A | 10/1996 | Chan |
| 5,569,306 A | 10/1996 | Thal |
| 5,572,770 A | 11/1996 | Boden |
| 5,575,801 A | 11/1996 | Habermeyer |
| 5,584,836 A | 12/1996 | Ballintyn |
| 5,584,839 A | 12/1996 | Gieringer |
| 5,601,557 A | 2/1997 | Hayhurst |
| 5,601,562 A | 2/1997 | Wolf |
| 5,620,012 A | 4/1997 | Benderev |
| 5,624,446 A | 4/1997 | Harryman, II |
| 5,630,824 A | 5/1997 | Hart |
| 5,637,112 A | 6/1997 | Moore |
| 5,643,321 A | 7/1997 | McDevitt |
| 5,645,568 A | 7/1997 | Chervitz |
| 5,647,874 A | 7/1997 | Hayhurst |
| 5,649,963 A | 7/1997 | McDevitt |
| 5,658,313 A | 8/1997 | Thal |
| 5,665,112 A | 9/1997 | Thal |
| 5,681,333 A | 10/1997 | Burkhart |
| 5,683,401 A | 11/1997 | Schmieding |
| 5,683,418 A | 11/1997 | Luscombe |
| 5,683,419 A | 11/1997 | Thal |
| 5,688,284 A | 11/1997 | Chervitz |
| 5,690,676 A | 11/1997 | DiPoto |
| 5,690,677 A | 11/1997 | Schmieding |
| 5,700,266 A | 12/1997 | Harryman, II |
| 5,702,397 A | 12/1997 | Goble |
| 5,702,398 A | 12/1997 | Tarabishy |
| 5,709,708 A | 1/1998 | Thal |
| 5,720,765 A | 2/1998 | Thal |
| 5,725,529 A | 3/1998 | Nicholson |
| 5,728,136 A | 3/1998 | Thal |
| 5,730,747 A | 3/1998 | Ek |
| 5,733,307 A | 3/1998 | Dinsdale |
| 5,746,754 A | 5/1998 | Chan |
| 5,746,763 A | 5/1998 | Benderev |
| 5,749,884 A | 5/1998 | Benderev |
| 5,755,728 A | 5/1998 | Maki |
| 5,766,221 A | 6/1998 | Benderev |
| 5,776,151 A | 7/1998 | Chan |
| 5,782,864 A | 7/1998 | Lizardi |
| 5,797,963 A | 8/1998 | McDevitt |
| 5,800,447 A | 9/1998 | Wenstrom, Jr. |
| 5,814,071 A | 9/1998 | McDevitt |
| 5,824,009 A | 10/1998 | Fukuda |
| RE36,020 E | 12/1998 | Moore |
| 5,842,478 A | 12/1998 | Benderev |
| 5,860,978 A | 1/1999 | McDevitt |
| 5,868,762 A | 2/1999 | Cragg |
| 5,891,150 A | 4/1999 | Chan |
| 5,891,168 A | 4/1999 | Thal |
| 5,895,425 A | 4/1999 | Grafton |
| 5,906,624 A | 5/1999 | Wenstrom, Jr. |
| 5,911,721 A | 6/1999 | Nicholson |
| 5,918,604 A | 7/1999 | Whelan |
| 5,935,129 A | 8/1999 | McDevitt |
| 5,938,686 A | 8/1999 | Benderev |
| 5,947,982 A | 9/1999 | Duran |
| 5,948,000 A | 9/1999 | Larsen |
| 5,957,924 A | 9/1999 | Tormala |
| 5,961,530 A | 10/1999 | Moore |
| 5,964,783 A | 10/1999 | Grafton |
| 5,968,044 A | 10/1999 | Nicholson |
| 5,980,558 A | 11/1999 | Wiley |
| 6,001,104 A | 12/1999 | Benderev |
| 6,024,758 A | 2/2000 | Thal |
| 6,029,805 A | 2/2000 | Alpern |
| 6,045,574 A | 4/2000 | Thal |
| 6,086,608 A | 7/2000 | Ek |
| 6,099,538 A | 8/2000 | Moses |
| 6,120,511 A | 9/2000 | Chan |
| 6,132,433 A | 10/2000 | Whelan |
| 6,143,017 A | 11/2000 | Thal |
| 6,156,039 A | 12/2000 | Thal |
| 6,183,479 B1 | 2/2001 | Törmälä |
| 6,267,766 B1 | 7/2001 | Burkhart |
| 6,290,711 B1 | 9/2001 | Caspari |
| 6,302,886 B1 | 10/2001 | McDevitt |
| 6,319,252 B1 | 11/2001 | McDevitt |
| 6,319,269 B1 | 11/2001 | Li |
| 6,368,335 B1 | 4/2002 | Chan |
| 6,371,124 B1 | 4/2002 | Whelan |
| 6,387,129 B2 | 5/2002 | Rieser |
| RE37,963 E | 1/2003 | Thal |
| 6,508,830 B2 | 1/2003 | Steiner |
| 6,511,487 B1 | 1/2003 | Oren |
| 6,514,274 B1 | 2/2003 | Boucher |
| 6,517,546 B2 | 2/2003 | Whittaker |
| 6,520,980 B1 | 2/2003 | Foerster |
| 6,524,316 B1 | 2/2003 | Nicholson |
| 6,524,317 B1 | 2/2003 | Ritchart |
| 6,527,794 B1 | 3/2003 | McDevitt |
| 6,527,795 B1 | 3/2003 | Lizardi |
| 6,537,319 B2 | 3/2003 | Whelan |
| 6,540,750 B2 | 4/2003 | Burkhart |
| 6,544,281 B2 | 4/2003 | ElAttrache |
| 6,547,807 B2 | 4/2003 | Chan |

(56) References Cited

U.S. PATENT DOCUMENTS

| | | |
|---|---|---|
| 6,585,730 B1 | 7/2003 | Foerster |
| 6,599,295 B1 | 7/2003 | Tornier |
| 6,605,096 B1 | 8/2003 | Ritchart |
| 6,610,064 B1 | 8/2003 | Goble |
| 6,616,674 B2 | 9/2003 | Schmieding |
| 6,623,524 B2 | 9/2003 | Schmieding |
| 6,629,984 B1 | 10/2003 | Chan |
| 6,638,283 B2 | 10/2003 | Thal |
| 6,641,596 B1 | 11/2003 | Lizardi |
| 6,641,597 B2 | 11/2003 | Burkhart |
| 6,645,227 B2 | 11/2003 | Fallin |
| 6,652,561 B1 | 11/2003 | Tran |
| 6,656,182 B1 | 12/2003 | Hayhurst |
| 6,656,183 B2 | 12/2003 | Colleran |
| 6,660,023 B2 | 12/2003 | McDevitt |
| 6,673,094 B1 | 1/2004 | McDevitt |
| 6,692,516 B2 | 2/2004 | West, Jr. |
| 6,712,849 B2 | 3/2004 | Re |
| 6,716,234 B2 | 4/2004 | Grafton |
| 6,723,107 B1 | 4/2004 | Skiba |
| 6,733,506 B1 | 5/2004 | McDevitt |
| 6,733,529 B2 | 5/2004 | Whelan |
| 6,743,233 B1 | 6/2004 | Baldwin |
| 6,770,073 B2 | 8/2004 | McDevitt |
| 6,770,076 B2 | 8/2004 | Foerster |
| 6,770,084 B1 | 8/2004 | Bain |
| 6,780,198 B1 | 8/2004 | Gregoire |
| 6,830,572 B2 | 12/2004 | McDevitt |
| 6,855,157 B2 | 2/2005 | Foerster |
| 6,860,887 B1 | 3/2005 | Frankle |
| 6,878,166 B2 | 4/2005 | Clark |
| 6,887,259 B2 | 5/2005 | Lizardi |
| 6,932,826 B2 | 8/2005 | Chan |
| 6,942,683 B2 | 9/2005 | Bonutti |
| 6,942,684 B2 | 9/2005 | Bonutti |
| 6,955,678 B2 | 10/2005 | Gabriel |
| 6,958,067 B2 | 10/2005 | Whittaker |
| 6,974,477 B2 | 12/2005 | Whelan |
| 6,984,237 B2 | 1/2006 | Hatch |
| 6,986,781 B2 | 1/2006 | Smith |
| 6,991,636 B2 | 1/2006 | Rose |
| 6,994,719 B2 | 2/2006 | Grafton |
| 6,994,725 B1 | 2/2006 | Goble |
| 7,029,490 B2 | 4/2006 | Grafton |
| 7,033,364 B1 | 4/2006 | Walters |
| 7,037,324 B2 | 5/2006 | Martinek |
| 7,063,724 B2 | 6/2006 | Re |
| 7,066,956 B2 | 6/2006 | Schmieding |
| 7,074,203 B1 | 7/2006 | Johanson |
| 7,077,863 B2 | 7/2006 | Schmieding |
| 7,081,126 B2 | 7/2006 | McDevitt |
| 7,083,638 B2 | 8/2006 | Foerster |
| 7,108,700 B2 | 9/2006 | Chan |
| 7,112,208 B2 | 9/2006 | Morris |
| 7,147,651 B2 | 12/2006 | Morrison |
| 7,172,595 B1 | 2/2007 | Goble |
| 7,175,632 B2 | 2/2007 | Singhatat |
| 7,195,642 B2 | 3/2007 | McKernan |
| 7,201,756 B2 | 4/2007 | Ross |
| 7,226,469 B2 | 6/2007 | Benavitz |
| 7,229,448 B2 | 6/2007 | Goble |
| 7,235,100 B2 | 6/2007 | Martinek |
| 7,247,164 B1 | 7/2007 | Ritchart |
| 7,285,124 B2 | 10/2007 | Foerster |
| 7,306,626 B2 | 12/2007 | Whelan |
| 7,309,337 B2 | 12/2007 | Colleran |
| 7,309,346 B2 | 12/2007 | Martinek |
| 7,329,272 B2 | 2/2008 | Burkhart |
| 7,341,592 B1 | 3/2008 | Walters |
| D569,973 S | 5/2008 | Oren |
| 7,377,926 B2 | 5/2008 | Topper |
| 7,381,212 B2 | 6/2008 | Topper |
| 7,381,213 B2 | 6/2008 | Lizardi |
| 7,399,302 B2 | 7/2008 | Goble |
| D576,277 S | 9/2008 | Oren |
| 7,458,975 B2 | 12/2008 | May |
| 7,465,308 B2 | 12/2008 | Sikora |
| 7,500,990 B2 | 3/2009 | Whelan |
| 7,517,357 B2 | 4/2009 | Abrams |
| 7,527,648 B2 | 5/2009 | May |
| 7,530,999 B2 | 5/2009 | Clark |
| 7,556,640 B2 | 7/2009 | Foerster |
| 7,569,059 B2 | 8/2009 | Cerundolo |
| 7,585,305 B2 | 9/2009 | Dreyfuss |
| 7,585,311 B2 | 9/2009 | Green |
| 7,588,587 B2 | 9/2009 | Barbieri |
| 7,588,595 B2 | 9/2009 | Miller |
| 7,594,917 B2 | 9/2009 | Whittaker |
| 7,608,084 B2 | 10/2009 | Oren |
| 7,625,386 B2 | 12/2009 | Abe |
| 7,637,926 B2 | 12/2009 | Foerster |
| 7,651,495 B2 | 1/2010 | McDevitt |
| 7,655,011 B2 | 2/2010 | Whittaker |
| 7,662,171 B2 | 2/2010 | West, Jr. |
| 7,674,275 B2 | 3/2010 | Martin |
| 7,674,290 B2 | 3/2010 | McKernan |
| 7,678,134 B2 | 3/2010 | Schmieding |
| 7,682,374 B2 | 3/2010 | Foerster |
| 7,695,494 B2 | 4/2010 | Foerster |
| 7,713,286 B2 | 5/2010 | Singhatat |
| 7,713,300 B2 | 5/2010 | Meridew |
| 7,749,237 B2 | 7/2010 | Chan |
| 7,771,441 B2 | 8/2010 | Cerundolo |
| 7,803,173 B2 | 9/2010 | Burkhart |
| 7,819,898 B2 | 10/2010 | Stone |
| 7,833,230 B2 | 11/2010 | Cerundolo |
| 7,833,244 B2 | 11/2010 | Cerundolo |
| 7,837,710 B2 | 11/2010 | Lombardo |
| 7,837,718 B2 | 11/2010 | Clark |
| 7,842,050 B2 | 11/2010 | Diduch |
| 7,867,251 B2 | 1/2011 | Colleran |
| 7,867,264 B2 | 1/2011 | McDevitt |
| 7,879,046 B2 | 2/2011 | Weinert |
| 7,879,048 B2 | 2/2011 | Bain |
| 7,883,519 B2 | 2/2011 | Oren |
| 7,892,256 B2 | 2/2011 | Grafton |
| 7,896,907 B2 | 3/2011 | McDevitt |
| 7,896,917 B2 | 3/2011 | Walters |
| 7,905,903 B2 | 3/2011 | Stone |
| 7,931,657 B2 | 4/2011 | Walters |
| 7,938,847 B2 | 5/2011 | Fanton |
| 7,942,914 B2 | 5/2011 | Cerundolo |
| 7,955,341 B2 | 6/2011 | Cerundolo |
| 7,959,649 B2 | 6/2011 | Burkhart |
| 7,959,650 B2 | 6/2011 | Kaiser |
| 7,963,972 B2 | 6/2011 | Foerster |
| 7,963,983 B2 | 6/2011 | Cerundolo |
| RE42,526 E | 7/2011 | Reiser |
| 7,976,565 B1 | 7/2011 | Meridew |
| 7,981,140 B2 | 7/2011 | Burkhart |
| 7,988,697 B2 | 8/2011 | Miller |
| 7,993,369 B2 | 8/2011 | Dreyfuss |
| 8,012,171 B2 | 9/2011 | Schmieding |
| 8,012,172 B2 | 9/2011 | Grafton |
| 8,012,174 B2 | 9/2011 | ElAttrache |
| 8,029,537 B2 | 10/2011 | West, Jr. |
| 8,038,652 B2 | 10/2011 | Morrison et al. |
| 8,043,308 B2 | 10/2011 | Bittenson |
| 8,062,295 B2 | 11/2011 | McDevitt |
| 8,080,013 B2 | 12/2011 | Whittaker |
| 8,083,769 B2 | 12/2011 | Cauldwell |
| 8,088,146 B2 | 1/2012 | Wert |
| 8,100,942 B1 | 1/2012 | Green |
| 8,105,343 B2 | 1/2012 | White |
| 8,109,966 B2 | 2/2012 | Ritchart |
| 8,109,969 B1 | 2/2012 | Green |
| 8,114,128 B2 | 2/2012 | Cauldwell |
| 8,118,835 B2 | 2/2012 | Weisel |
| 8,128,634 B2 | 3/2012 | Whittaker |
| 8,133,258 B2 | 3/2012 | Foerster |
| 8,137,360 B2 | 3/2012 | Whittaker |
| 8,137,381 B2 | 3/2012 | Foerster |
| 8,137,383 B2 | 3/2012 | West, Jr. |
| 8,147,505 B2 | 4/2012 | Delli-Santi |

(56) References Cited

U.S. PATENT DOCUMENTS

| | | |
|---|---|---|
| 8,162,978 B2 | 4/2012 | Lombardo |
| 8,167,906 B2 | 5/2012 | Cauldwell |
| 8,177,796 B2 | 5/2012 | Akyuz |
| 8,202,295 B2 | 6/2012 | Kaplan |
| 8,202,296 B2 | 6/2012 | Burkhart |
| 8,202,297 B2 | 6/2012 | Burkhart |
| 8,226,716 B2 | 7/2012 | Mckernan |
| 8,231,653 B2 | 7/2012 | Dreyfuss |
| 8,262,675 B2 | 9/2012 | Cropper |
| 8,267,964 B2 | 9/2012 | Green |
| 8,277,458 B2 | 10/2012 | Schneider |
| 8,277,464 B2 | 10/2012 | Bittenson |
| 8,277,484 B2 | 10/2012 | Barbieri |
| 8,282,643 B2 | 10/2012 | Dross |
| 8,282,659 B2 | 10/2012 | Oren |
| 8,298,262 B2 | 10/2012 | Stone |
| 8,317,829 B2 | 11/2012 | Foerster |
| 8,317,862 B2 | 11/2012 | Troger |
| 8,328,843 B2 | 12/2012 | Oren |
| 8,348,975 B2 | 1/2013 | Dreyfuss |
| 8,361,079 B2 | 1/2013 | Pandya |
| 8,372,124 B2 | 2/2013 | Paulk |
| 8,382,835 B2 | 2/2013 | Meridew |
| 8,383,188 B2 | 2/2013 | Mazzocca |
| 8,388,654 B2 | 3/2013 | Snyder |
| 8,394,112 B2 | 3/2013 | Nason |
| 8,394,123 B2 | 3/2013 | Cauldwell |
| 8,409,204 B2 | 4/2013 | Martin |
| 8,409,225 B2 | 4/2013 | Bull |
| 8,419,794 B2 | 4/2013 | ElAttrache |
| 8,425,536 B2 | 4/2013 | Foerster |
| 8,430,909 B2 | 4/2013 | Dreyfuss |
| 8,435,264 B2 | 5/2013 | Sojka |
| 8,444,672 B2 | 5/2013 | Foerster |
| 8,444,674 B2 | 5/2013 | Kaplan |
| 8,449,552 B2 | 5/2013 | Sanders |
| 8,454,654 B2 | 6/2013 | Ferragamo |
| 8,460,340 B2 | 6/2013 | Sojka |
| 8,465,521 B2 | 6/2013 | Cook |
| 8,465,522 B2 | 6/2013 | Burkhart |
| 8,469,998 B2 | 6/2013 | Sojka |
| 8,491,595 B2 | 7/2013 | Volpi |
| 8,491,600 B2 | 7/2013 | McDevitt |
| 8,506,596 B2 | 8/2013 | Stone |
| 8,512,378 B2 | 8/2013 | Green |
| 8,518,091 B2 | 8/2013 | McDevitt |
| 8,523,902 B2 | 9/2013 | Heaven |
| 8,529,577 B2 | 9/2013 | Hirt |
| 8,529,601 B2 | 9/2013 | Green |
| 8,535,350 B2 | 9/2013 | Lizardi |
| 8,540,732 B2 | 9/2013 | Weinert |
| 8,540,737 B2 | 9/2013 | Chudik |
| 8,551,123 B2 | 10/2013 | Pandya |
| 8,556,911 B2 | 10/2013 | Mehta |
| 8,579,974 B2 | 11/2013 | Pandya |
| 8,591,580 B2 | 11/2013 | Mckernan |
| 8,597,328 B2 | 12/2013 | Cauldwell |
| 8,613,756 B2 | 12/2013 | Lizardi |
| 8,617,186 B2 | 12/2013 | White |
| 8,617,219 B2 | 12/2013 | Oren |
| 8,623,032 B2 | 1/2014 | Diduch |
| 8,652,171 B2 | 2/2014 | Stone |
| 8,657,854 B2 | 2/2014 | Foerster |
| 8,663,279 B2 | 3/2014 | Burkhart |
| 8,663,280 B2 | 3/2014 | Kaplan |
| 8,672,954 B2 | 3/2014 | Oren |
| 8,672,966 B2 | 3/2014 | Wert |
| 8,672,967 B2 | 3/2014 | DiMatteo |
| 8,672,970 B2 | 3/2014 | Ferragamo |
| 8,685,060 B2 | 4/2014 | Foerster |
| 8,690,915 B2 | 4/2014 | Hootstein |
| 8,696,688 B2 | 4/2014 | Stone |
| 8,702,752 B2 | 4/2014 | Schmieding |
| 8,702,754 B2 | 4/2014 | DiMatteo |
| 8,709,040 B2 | 4/2014 | Anderhub |
| 8,709,395 B2 | 4/2014 | Boutros |
| 8,721,650 B2 | 5/2014 | Fanton |
| 8,740,913 B2 | 6/2014 | Schneider |
| 8,747,469 B2 | 6/2014 | Wang |
| 8,764,798 B2 | 7/2014 | Housman |
| 8,771,315 B2 | 7/2014 | Lunn |
| 8,771,351 B2 | 7/2014 | ElAttrache |
| 8,777,990 B2 | 7/2014 | van der Burg et al. |
| 8,784,449 B2 | 7/2014 | Snyder |
| 8,784,489 B2 | 7/2014 | Walters |
| 8,790,370 B2 | 7/2014 | Spenciner |
| 8,808,326 B2 | 8/2014 | Gagliano |
| 8,814,905 B2 | 8/2014 | Sengun |
| 8,828,029 B2 | 9/2014 | White |
| 8,834,495 B2 | 9/2014 | White |
| 8,834,521 B2 | 9/2014 | Pinto |
| 8,834,543 B2 | 9/2014 | McDevitt |
| 8,858,560 B2 | 10/2014 | Bradley |
| 8,870,877 B2 | 10/2014 | Koogle, Jr. |
| 8,881,635 B2 | 11/2014 | Martin |
| 8,882,801 B2 | 11/2014 | DiMatteo |
| 8,906,060 B2 | 12/2014 | Hart |
| 8,926,663 B2 | 1/2015 | Green |
| 8,936,620 B2 | 1/2015 | Kaiser |
| 8,943,941 B2 | 2/2015 | Dow |
| 8,951,292 B2 | 2/2015 | Paulk |
| 8,961,576 B2 | 2/2015 | Hodge |
| 8,986,345 B2 | 3/2015 | Denham |
| 8,986,346 B2 | 3/2015 | Dreyfuss |
| 8,986,347 B2 | 3/2015 | Housman |
| 8,992,573 B2 | 3/2015 | Van Der Burg |
| 9,005,246 B2 | 4/2015 | Burkhart |
| 9,017,381 B2 | 4/2015 | Kaiser |
| 9,023,083 B2 | 5/2015 | Foerster |
| 9,034,014 B2 | 5/2015 | Catania |
| 9,044,222 B2 | 6/2015 | Dross |
| 9,044,226 B2 | 6/2015 | Green |
| 9,107,653 B2 | 8/2015 | Sullivan |
| 9,113,859 B2 | 8/2015 | Dooney, Jr. |
| 9,144,425 B2 | 9/2015 | Kaplan |
| 9,149,268 B2 | 10/2015 | Graul |
| 9,155,542 B2 | 10/2015 | Markarian |
| 9,161,750 B2 | 10/2015 | Zirps |
| 9,179,907 B2 | 11/2015 | ElAttrache |
| 9,198,649 B2 | 12/2015 | Karapetian |
| 9,226,742 B2 | 1/2016 | Wolf |
| 9,265,496 B2 | 2/2016 | Sojka |
| 9,445,805 B2 | 9/2016 | Snell |
| 9,498,232 B2 | 11/2016 | Perez, III |
| 2001/0016747 A1 | 8/2001 | Romano |
| 2002/0029066 A1 | 3/2002 | Foerster |
| 2002/0065526 A1 | 5/2002 | Oren |
| 2003/0105524 A1 | 6/2003 | Paulos |
| 2003/0171778 A1 | 9/2003 | Lizardi |
| 2003/0195528 A1 | 10/2003 | Ritchart |
| 2003/0195563 A1 | 10/2003 | Foerster |
| 2003/0229362 A1 | 12/2003 | Chan et al. |
| 2004/0010286 A1 | 1/2004 | Gieringer |
| 2004/0082956 A1 | 4/2004 | Baldwin |
| 2004/0088004 A1 | 5/2004 | Rosch |
| 2004/0098051 A1 | 5/2004 | Fallin |
| 2004/0098053 A1 | 5/2004 | Tran |
| 2004/0116843 A1 | 6/2004 | Chan |
| 2004/0172062 A1 | 9/2004 | Burkhart |
| 2004/0267317 A1 | 12/2004 | Higgins |
| 2005/0033362 A1 | 2/2005 | Grafton |
| 2005/0033364 A1 | 2/2005 | Gregoire |
| 2005/0149122 A1 | 7/2005 | McDevitt |
| 2005/0245932 A1 | 11/2005 | Fanton |
| 2005/0277986 A1 | 12/2005 | Foerster |
| 2006/0074438 A1 | 4/2006 | Chan |
| 2006/0079904 A1 | 4/2006 | Thal |
| 2006/0142784 A1 | 6/2006 | Kontos |
| 2006/0149258 A1 | 7/2006 | Sousa |
| 2006/0155328 A1 | 7/2006 | Foerster |
| 2006/0241619 A1* | 10/2006 | Cerundolo ......... A61B 17/0401 623/13.14 |
| 2006/0241658 A1 | 10/2006 | Cerundolo |
| 2006/0247641 A1 | 11/2006 | Re |

(56) References Cited

U.S. PATENT DOCUMENTS

| | | |
|---|---|---|
| 2006/0271060 A1 | 11/2006 | Gordon |
| 2006/0282081 A1 | 12/2006 | Fanton |
| 2006/0282082 A1 | 12/2006 | Fanton |
| 2006/0282083 A1 | 12/2006 | Fanton |
| 2006/0293710 A1* | 12/2006 | Foerster ............ A61B 17/0401 606/232 |
| 2007/0005067 A1 | 1/2007 | Dross |
| 2007/0005068 A1 | 1/2007 | Sklar |
| 2007/0016251 A1 | 1/2007 | Roby |
| 2007/0021751 A1 | 1/2007 | Reay-Young |
| 2007/0027475 A1 | 2/2007 | Pagedas |
| 2007/0088362 A1 | 4/2007 | Bonutti |
| 2007/0156149 A1 | 7/2007 | Fanton |
| 2007/0156150 A1 | 7/2007 | Fanton |
| 2007/0156176 A1 | 7/2007 | Fanton |
| 2007/0167950 A1 | 7/2007 | Tauro |
| 2007/0173845 A1 | 7/2007 | Kim |
| 2007/0203498 A1 | 8/2007 | Gerber |
| 2007/0213730 A1 | 9/2007 | Martinek |
| 2007/0213770 A1 | 9/2007 | Dreyfuss |
| 2007/0219557 A1 | 9/2007 | Bourque |
| 2007/0219558 A1 | 9/2007 | Deutsch |
| 2007/0288023 A1 | 12/2007 | Pellegrino |
| 2008/0009904 A1 | 1/2008 | Bourque |
| 2008/0033486 A1 | 2/2008 | Whittaker |
| 2008/0057838 A1 | 3/2008 | Huang |
| 2008/0077161 A1 | 3/2008 | Kaplan |
| 2008/0103528 A1 | 5/2008 | Zirps |
| 2008/0125815 A1 | 5/2008 | Heaven |
| 2008/0147063 A1* | 6/2008 | Cauldwell .......... A61B 17/0401 606/60 |
| 2008/0188936 A1 | 8/2008 | Ball |
| 2008/0208253 A1 | 8/2008 | Dreyfuss |
| 2008/0234730 A1 | 9/2008 | Cotton |
| 2008/0243174 A1 | 10/2008 | Oren |
| 2008/0243177 A1 | 10/2008 | Oren |
| 2008/0243178 A1 | 10/2008 | Oren |
| 2008/0275453 A1 | 11/2008 | Lafosse |
| 2008/0287992 A1 | 11/2008 | Tornier |
| 2008/0300629 A1 | 12/2008 | Surti |
| 2009/0018561 A1 | 1/2009 | Schwartz |
| 2009/0018581 A1 | 1/2009 | Anderson |
| 2009/0036905 A1 | 2/2009 | Schmieding |
| 2009/0048623 A1 | 2/2009 | Lafosse |
| 2009/0062819 A1 | 3/2009 | Burkhart |
| 2009/0076544 A1 | 3/2009 | DiMatteo |
| 2009/0099598 A1 | 4/2009 | McDevitt |
| 2009/0138002 A1 | 5/2009 | Fenton |
| 2009/0149884 A1 | 6/2009 | Snyder |
| 2009/0171360 A1 | 7/2009 | Whelan |
| 2009/0187216 A1 | 7/2009 | Schmieding |
| 2009/0192546 A1 | 7/2009 | Schmieding |
| 2009/0222039 A1 | 9/2009 | Dreyfuss |
| 2009/0287246 A1 | 11/2009 | Cauldwell |
| 2009/0292313 A1 | 11/2009 | Anspach, III |
| 2009/0312782 A1 | 12/2009 | Park |
| 2009/0312794 A1 | 12/2009 | Nason |
| 2009/0318960 A1 | 12/2009 | Burkhart |
| 2010/0004683 A1 | 1/2010 | Hoof |
| 2010/0087872 A1 | 4/2010 | Morihara |
| 2010/0100129 A1 | 4/2010 | West, Jr. |
| 2010/0121337 A1 | 5/2010 | Pandya |
| 2010/0121348 A1 | 5/2010 | van der Burg |
| 2010/0121375 A1 | 5/2010 | Pandya |
| 2010/0137889 A1 | 6/2010 | Oren |
| 2010/0179573 A1 | 7/2010 | Levinsohn |
| 2010/0198235 A1 | 8/2010 | Pierce |
| 2010/0249835 A1 | 9/2010 | Schwartz |
| 2010/0262184 A1 | 10/2010 | Dreyfuss |
| 2010/0292732 A1* | 11/2010 | Hirotsuka .......... A61B 17/0401 606/232 |
| 2010/0318125 A1 | 12/2010 | Gerber |
| 2010/0318139 A1 | 12/2010 | Beauchamp |
| 2010/0324575 A1 | 12/2010 | Chan |
| 2011/0009867 A1* | 1/2011 | Oren .................. A61B 17/0482 606/80 |
| 2011/0009884 A1 | 1/2011 | Kaplan |
| 2011/0022087 A1 | 1/2011 | Cerundolo |
| 2011/0028997 A1 | 2/2011 | Gregoire |
| 2011/0071550 A1 | 3/2011 | Diduch |
| 2011/0106013 A1 | 5/2011 | Whittaker |
| 2011/0106124 A1 | 5/2011 | Beauchamp |
| 2011/0112550 A1 | 5/2011 | Heaven |
| 2011/0112576 A1 | 5/2011 | Nguyen |
| 2011/0118757 A1 | 5/2011 | Pierce |
| 2011/0118762 A1 | 5/2011 | Dooney, Jr. |
| 2011/0152928 A1 | 6/2011 | Colleran |
| 2011/0190815 A1 | 8/2011 | Saliman |
| 2011/0208198 A1 | 8/2011 | Anderson |
| 2011/0224726 A1 | 9/2011 | Lombardo |
| 2011/0238111 A1 | 9/2011 | Frank |
| 2011/0238112 A1 | 9/2011 | Kim |
| 2011/0238113 A1 | 9/2011 | Fanton |
| 2011/0245869 A1 | 10/2011 | Burkhart |
| 2011/0301622 A1 | 12/2011 | Oren |
| 2012/0041484 A1 | 2/2012 | Briganti |
| 2012/0059415 A1 | 3/2012 | Sklar |
| 2012/0116451 A1 | 5/2012 | Tepic |
| 2012/0143224 A1 | 6/2012 | Chan |
| 2012/0150225 A1 | 6/2012 | Burkhart |
| 2012/0150235 A1 | 6/2012 | Snyder |
| 2012/0158051 A1 | 6/2012 | Foerster |
| 2012/0165868 A1 | 6/2012 | Burkhart |
| 2012/0179200 A1 | 7/2012 | Cauldwell |
| 2012/0197296 A1 | 8/2012 | Mayer |
| 2012/0209279 A1 | 8/2012 | Snyder |
| 2012/0209325 A1 | 8/2012 | Gagliano |
| 2012/0245634 A1 | 9/2012 | Kaplan |
| 2012/0265219 A1 | 10/2012 | Rushdy |
| 2012/0272816 A1 | 11/2012 | Ueda |
| 2013/0023928 A1 | 1/2013 | Dreyfuss |
| 2013/0023929 A1 | 1/2013 | Sullivan |
| 2013/0023930 A1 | 1/2013 | Stone |
| 2013/0035720 A1 | 2/2013 | Perriello |
| 2013/0060280 A1 | 3/2013 | Wolf |
| 2013/0096611 A1 | 4/2013 | Sullivan |
| 2013/0103083 A1 | 4/2013 | Baird |
| 2013/0123809 A1 | 5/2013 | Murphy |
| 2013/0123840 A1 | 5/2013 | Murphy |
| 2013/0123842 A1 | 5/2013 | Chan |
| 2013/0123843 A1 | 5/2013 | Chan |
| 2013/0144335 A1 | 6/2013 | Sandow |
| 2013/0150885 A1 | 6/2013 | Dreyfuss |
| 2013/0165972 A1 | 6/2013 | Sullivan |
| 2013/0178854 A1 | 7/2013 | Sholev |
| 2013/0190782 A1 | 7/2013 | Nason |
| 2013/0190871 A1 | 7/2013 | Markarian |
| 2013/0197575 A1 | 8/2013 | Karapetian |
| 2013/0197577 A1 | 8/2013 | Wolf |
| 2013/0197578 A1 | 8/2013 | Gregoire |
| 2013/0204253 A1 | 8/2013 | Oren |
| 2013/0204299 A1 | 8/2013 | Mantovani |
| 2013/0211429 A1 | 8/2013 | Snyder |
| 2013/0218273 A1 | 8/2013 | Bull |
| 2013/0226231 A1 | 8/2013 | Weinert |
| 2013/0267998 A1 | 10/2013 | Vijay |
| 2013/0296936 A1 | 11/2013 | Burkhart |
| 2013/0325011 A1 | 12/2013 | Cleveland |
| 2013/0338710 A1 | 12/2013 | Heaven |
| 2013/0345711 A1 | 12/2013 | Mehta |
| 2013/0345749 A1 | 12/2013 | Sullivan |
| 2013/0345750 A1 | 12/2013 | Sullivan |
| 2014/0046369 A1 | 2/2014 | Heaven |
| 2014/0046443 A1 | 2/2014 | Mckernan |
| 2014/0081320 A1 | 3/2014 | Sengun |
| 2014/0107700 A1 | 4/2014 | Baird |
| 2014/0114317 A1 | 4/2014 | Oren |
| 2014/0114411 A1 | 4/2014 | Baird |
| 2014/0121467 A1 | 5/2014 | Vayser |
| 2014/0134802 A1 | 5/2014 | Lin |
| 2014/0135802 A1 | 5/2014 | Mantovani |
| 2014/0163612 A1 | 6/2014 | Hootstein |
| 2014/0171948 A1 | 6/2014 | Griffiths |

(56) References Cited

U.S. PATENT DOCUMENTS

| | | |
|---|---|---|
| 2014/0172016 A1 | 6/2014 | Housman |
| 2014/0186416 A1 | 7/2014 | Boutros |
| 2014/0186418 A1 | 7/2014 | Boutros |
| 2014/0194906 A1 | 7/2014 | Topper |
| 2014/0207189 A1 | 7/2014 | Foerster |
| 2014/0214038 A1 | 7/2014 | Sholev |
| 2014/0222072 A1 | 8/2014 | Gerber |
| 2014/0243892 A1 | 8/2014 | Choinski |
| 2014/0257384 A1 | 9/2014 | Dreyfuss |
| 2014/0288594 A1 | 9/2014 | Shaefers |
| 2014/0303625 A1 | 10/2014 | Sholev |
| 2014/0324100 A1 | 10/2014 | Burkhart |
| 2014/0343605 A1 | 11/2014 | Lunn |
| 2014/0364876 A1 | 12/2014 | White |
| 2014/0364905 A1 | 12/2014 | Lunn |
| 2014/0364907 A1 | 12/2014 | White |
| 2014/0379027 A1 | 12/2014 | Dreyfuss |
| 2014/0379028 A1 | 12/2014 | Lo |
| 2015/0005773 A1 | 1/2015 | Oren |
| 2015/0005817 A1 | 1/2015 | Snyder |
| 2015/0005818 A1 | 1/2015 | McDevitt |
| 2015/0025552 A1 | 1/2015 | Stoll |
| 2015/0032155 A1 | 1/2015 | Dreyfuss |
| 2015/0032157 A1 | 1/2015 | Dooney, Jr. |
| 2015/0045795 A1 | 2/2015 | Sholev |
| 2015/0051645 A1 | 2/2015 | Green |
| 2015/0066079 A1 | 3/2015 | Schmieding |
| 2015/0066080 A1 | 3/2015 | Olson |
| 2015/0066081 A1 | 3/2015 | Martin |
| 2015/0088196 A1 | 3/2015 | Kaplan |
| 2015/0119937 A1 | 4/2015 | Lunn |
| 2015/0141998 A1 | 5/2015 | Kiapour |
| 2015/0150551 A1 | 6/2015 | Paulk |
| 2015/0157312 A1 | 6/2015 | Burkhart |
| 2015/0196388 A1 | 7/2015 | Housman |
| 2015/0216522 A1 | 8/2015 | Ticker |
| 2015/0223926 A1 | 8/2015 | Foerster |
| 2015/0245831 A1 | 9/2015 | Sullivan |
| 2015/0297211 A1 | 10/2015 | Sullivan |
| 2015/0297274 A1 | 10/2015 | Dreyfuss |
| 2015/0313586 A1 | 11/2015 | Burkhart |
| 2015/0327849 A1 | 11/2015 | Dooney, Jr. |
| 2015/0335327 A1 | 11/2015 | Ferguson |
| 2015/0351752 A1 | 12/2015 | Rousseau |
| 2015/0359533 A1 | 12/2015 | Kaplan |
| 2016/0015380 A1 | 1/2016 | Sholev |
| 2016/0296224 A1 | 10/2016 | Snell |
| 2016/0338689 A1 | 11/2016 | Baird |
| 2016/0338693 A1 | 11/2016 | Graul |

FOREIGN PATENT DOCUMENTS

| | | | |
|---|---|---|---|
| WO | WO2004049958 A1 | 6/2004 | |
| WO | WO2009018565 A1 | 2/2009 | |
| WO | WO2009042951 A1 | 4/2009 | |
| WO | WO2009055800 A1 | 4/2009 | |
| WO | WO2009076526 A1 | 6/2009 | |
| WO | WO2010005749 A1 | 1/2010 | |
| WO | WO2010009217 A1 | 1/2010 | |
| WO | WO2010056786 A2 | 5/2010 | |
| WO | WO2010056787 A2 | 5/2010 | |
| WO | WO2011056701 A1 | 5/2011 | |
| WO | WO2011059995 A2 | 5/2011 | |
| WO | WO2011060022 A2 | 5/2011 | |
| WO | WO2011060437 A1 | 5/2011 | |
| WO | WO2011133233 A1 | 10/2011 | |
| WO | WO2012024446 A2 | 2/2012 | |
| WO | WO2012052891 A1 | 4/2012 | |
| WO | WO2012129388 A1 | 9/2012 | |
| WO | WO2013014553 A1 | 1/2013 | |
| WO | WO2013027210 A1 | 2/2013 | |
| WO | WO2013052128 A1 | 4/2013 | |
| WO | WO2013112449 A1 | 8/2013 | |
| WO | WO2013151817 A1 | 10/2013 | |
| WO | WO2013181212 A1 | 12/2013 | |
| WO | WO2014051930 A2 | 4/2014 | |
| WO | WO2014055678 A1 | 4/2014 | |
| WO | WO2014059378 A1 | 4/2014 | |
| WO | WO2014066116 A1 | 5/2014 | |
| WO | WO2014071052 A1 | 5/2014 | |
| WO | WO2014071066 A1 | 5/2014 | |
| WO | WO2014018946 A9 | 12/2014 | |
| WO | WO2015005951 A1 | 1/2015 | |
| WO | WO2015008176 A2 | 1/2015 | |
| WO | WO2015017426 A1 | 2/2015 | |
| WO | WO2015031559 A1 | 3/2015 | |
| WO | WO2016148941 A1 | 9/2016 | |

OTHER PUBLICATIONS

Carter, Sally L., et al, "Suture Performance in Standard Arthroscopic Knots—Effects of Material and Design" Smith & Nephew, Inc., www.smith-nephew.com, 2004, 4 pp.

OPUS AutoCuff Magnum X Knotless Fixation Implant with Independent Tensioning, ArthroCare Sports Medicine, www.arthrocaresportsmedicine.com, 2009, 2 pp.

The OPUS AutoCuff System for Rotatpr Cuff Repair, ArthroCare Sports Medicine, www.arthrocaresportsmedicine.com, 2006, 8 pp.

The OPUS TwinLock Knotless Fixation System, ArthroCare Sports Medicine, www.arthrocaresportsmedicine.com, 2010, 2 pp.

BioRaptor Knotless Suture Anchor, Smith & Nephew, Inc., www.smith-newphew.com, 2010, 6 pp.

Arthroscopic Shoulder Repair Using the Smith & Nephew Footpring PK Suture Anchor, Smith & Nephew, Inc., www.smith-nephew.com, 2008, 12 pp.

Dr. S. D. Gerber Double Row Method Surgical Technique, Stryker Corporation, www.stryker.com, 2010, 12 pp.

Multifix's Peek 5.5mm and 6.5mm Knotless Implants Technique Guide, ArthroCare Corporation, www.smith-nephew.com, 2015, 8 pp.

The Fully Threaded Family of Soft Tissue Repair Anchors, Arthrex, Inc., www.arthrex.com, 2012, 6 pp.

2.5 mm PushLock Knotless Suture Anchor, Arthrex, Inc., www.arthrex.com, 2013, 2 pp.

Achilles SpeedBridge Surgical Technique, Arthrex, Inc., www.arthrex.com, 2013, 6 pp.

Biceps Tenodesis SwiveLock System Surgical Technique, Arthrex, Inc., www.arthrex.com, 2012, 6 pp.

Revolutionizing Orthopedic Surgery, FiberWire Braided Composite Suture, Arthrex, Inc., www.arthrex.com, 2012, 8 pp.

Massive Rotator Cuff Repair and Augmentation using the SpeedBridge and ArthroFlex Dermal Matrix Surgical Technique, Arthrex, Inc., www.arthrex.com, 2012, 4 pp.

Arthrex SpeedBridge and Tornier Arthro Tunneler Biomechanical Cadavar Testing, Arthrex, Inc., 2010, 2 pp.

SpeedBridge and SpeedFix Knotless Rotator Cuff Repair using the SwiveLock C and FiberTape Surgical Technique, Arthrex, Inc., www.arthrex.com, 2013, 8 pp.

Double Row Rotator Cuff Repair using the Bio-Corkscrew FT Surgical Technique, Arthrex, Inc. www.arthrex.com, 2007, 6 pp.

SutureBridge Double Row Rotator Cuff Repair Surgical Technique, Arthrex, Inc., www.arthrex.com, 2013, 6 pp.

SwiveLock and FiberChain Knotless Rotator Cuff Repair Surgical Technique, Arthrex, Inc, www.arthrex.com, 2011, 8 pp.

The Next Generation in Shoulder & Elbow Repair and Reconstruction Technology, Arthrex, Inc., www.arthrex.com, 2014, 56 pp.

The Next Generation in Shoulder & Elbow Repair and Reconstruction Technology, Arthrex, Inc., www.arthrex.com, 2015, 56 pp.

Achilles SutureBridge Surgical Technique, Arthrex, Inc., www.arthrex.com, 2014, 6 pp.

Arthrex is Reaching New Heights in Rotator Cuff Repair, Arthrex, Inc., www.arthrex.com, 2007, 8 pp.

Quattro Shoulder System—Innovative Rotator Cuff Solutions, Cayenne Medical, Inc., www.cayennemedical.com, 6 pp.

Chu, T., et al., "Biomechanical Evaluation of Knotless Fixation Systems for Rotator Cuff Repairs", 56th Annual Meeting of the Orthopaedic Research Society, Post No. 1791, 1 pp.

(56) References Cited

OTHER PUBLICATIONS

Flores, Steve, "Comparison of the Pull-Back Effect of Rotator Cuff Anchors", Arthrex, Inc., 2007, 2 pp.
Shoulder Restoration System, PopLok Knotless Suture Anchor, ConMed Linvatec, www.linvatec.com, 8 pp.
Shoulder Restoration System, ConMed Linvatec, www.linvatec.com, 2014, 20 pp.
Defranco, Michael J., et al., "Arthroscopic Rotator Cuff Repair Failure Resulting from Decorticiation of the Rotator Cuff Footprint: A Case Report", The American Journal of Orthopedics, Dec. 2009, pp. 32-33.
Halbrecht, Jeffrey, "Versalok a New Technique for Arthroscopic Knotless Rotator Cuff Repair", 44 pp.
Versalok, The Next Generation in Rotator Cuff Repair, DePuy Mitek, 15 pp.
Introducing the Healix Advance Family of Suture Anchors, DePuy Mitek, Inc, 2012, 4 pp.
Versalok Peek, The New, 100% Radiolucent, Self-Punching, Knotless Anchor, DePuy Mitek, Inc., 2010, 4 pp.
The Next Generation in Rotator Cuff Repair, DePuy Mitek, Inc., 2007, 18 pp.
Efird, Chad, et al., "Knotless Single-Row Rotator Cuff Repair: A Comparative Biomechanical Study of 2 Knotless Suture Anchors", Healio.com/Orthopedics, Aug. 2013, 5 pp.
Arthroscopic Shoulder Repair Using the Smith & Nephew Footprint PK Suture Anchor, Smith & Nephew, Inc., 2008, 12 pp.
Knotless SutureTak Instability Repair Surgical Technique, Arthrex, Inc., www.arthrex.com, 2015, 6 pp.
Mall, Nathan A., et al., "Transosseous-Equivalent Rotator Cuff Repair: A Systematic Review on the Biomechanical Importance of Tying the Medial Row", Arthroscopy: The Journal of Arthroscopic and Related Surgery, vol. 29, No. 2, Feb. 2013, pp. 377-386.
Surgical Technique Sharc-FT and Taylor Stitcher Transosseus Devices for Fast Rotator Cuff Repair, NCS Lab Medical Devices Factory, 12 pp.
Nho, Shane J., et al,. "Bioabsorbable Anchors in Glenohumeral Shoulder Surgery", Arthrscopy: The Journal of Arthroscopic and Related Surgery, vol. 25, No. 7, Jul. 2009, pp. 788-793.
Cinch Lock SS (Sports Sheath) Knotless Labrum Restoration, Stryker Corporation, www.stryker.com, 6 pp.
ReelX STT Knotless Anchor System, Stryker Corporation, www.stryker.com, 2010, 4 pp.
ArthroTunneler TunnelPro System, Transosseous Rotator Cuff Repair, Tornier, Inc., www.tornier.com, 2012, 6 pp.
Pull-Out Strength Comparison of Arthrex to Mitek Suture Anchors, Arthrex Research and Development, Arthrex, Inc., 2010, 1 pp.
Quickdraw Knotless Suture Anchor System Surgical Technique, Wrìtght Medical Technology, Inc. www.wmt.com, 2011, 28 pp.
The DoublePlay Biocomposite Suture Anchor, ArthroCare Sports Medicine, www.arthrocaresportsmedicine.com, 2009, 12 pp.
ALLThread Knotless Suture Anchor, Double Row Rotator Cuff Repair, Biomet Orthopedics, www.biomet.com, 2012, 12 pp.
Arthroscopic and Mini-Open Rotator Cuff Repair Using JuggerKnot Soft Anchor—2.9 mm with ALLthread Knotless Anchor Surgical Technique, Biomet Sports Medicine, www.biomet.com, 2013, 16 pp.

\* cited by examiner

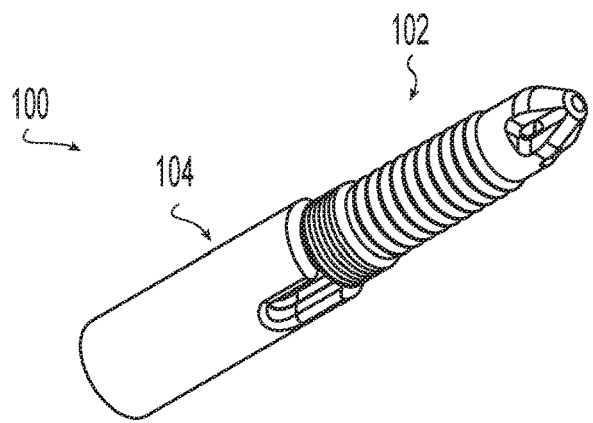
Fig. 1
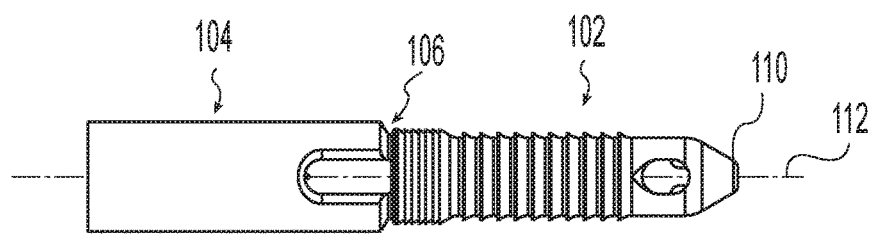
Fig. 2
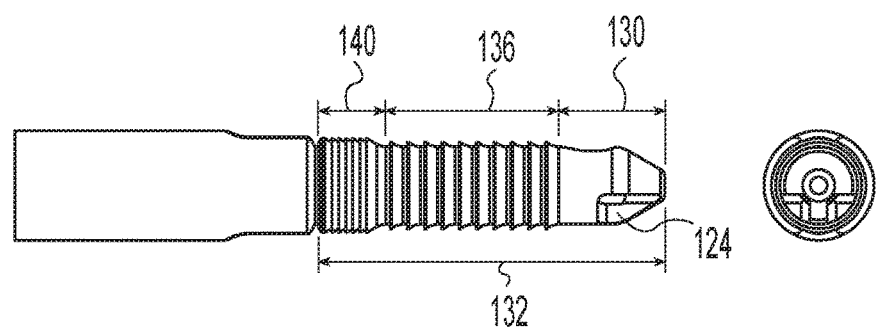
Fig. 3　　　Fig. 4　　　Fig. 5
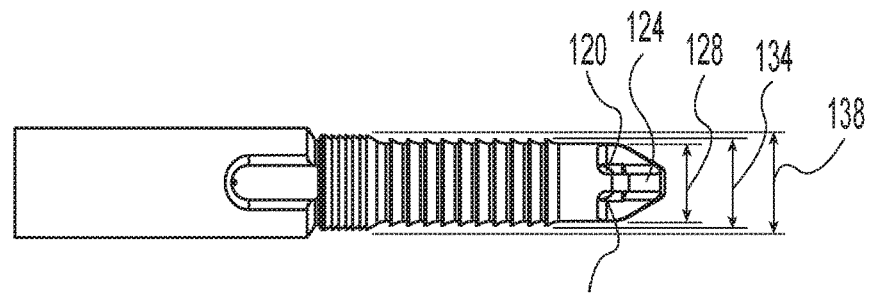
Fig. 6

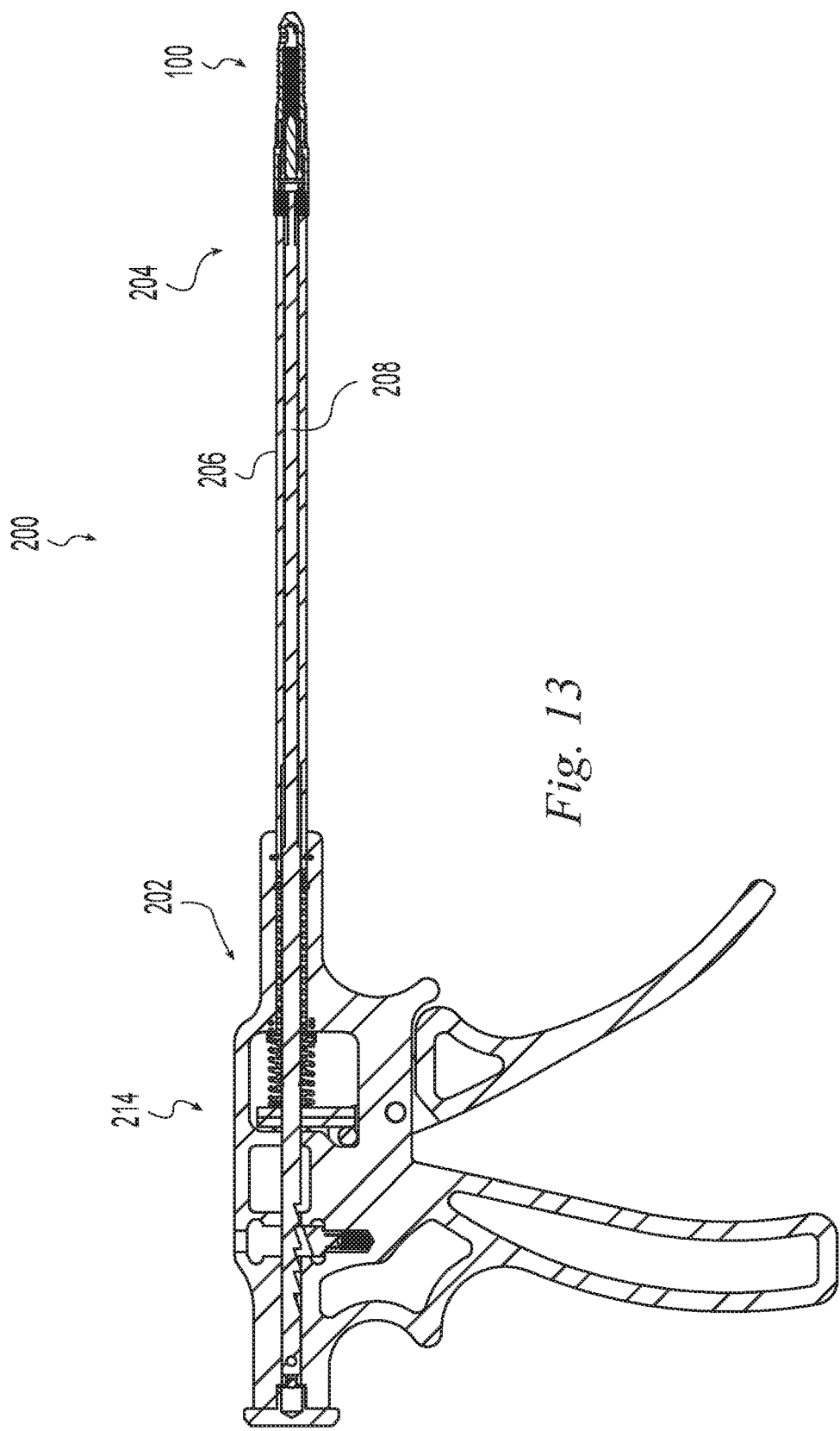

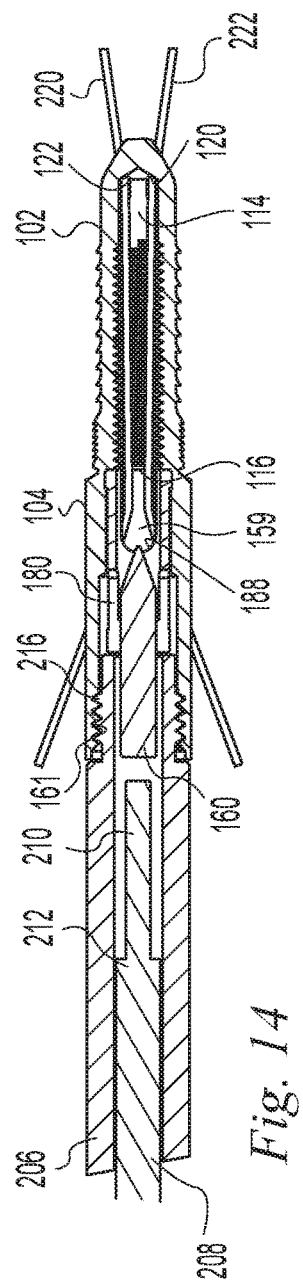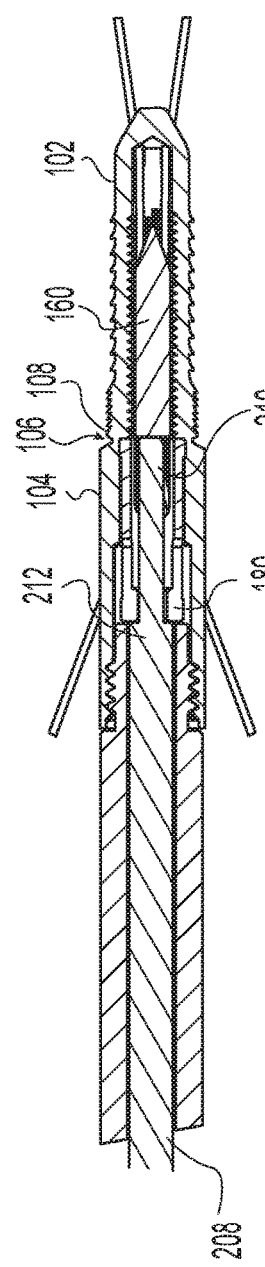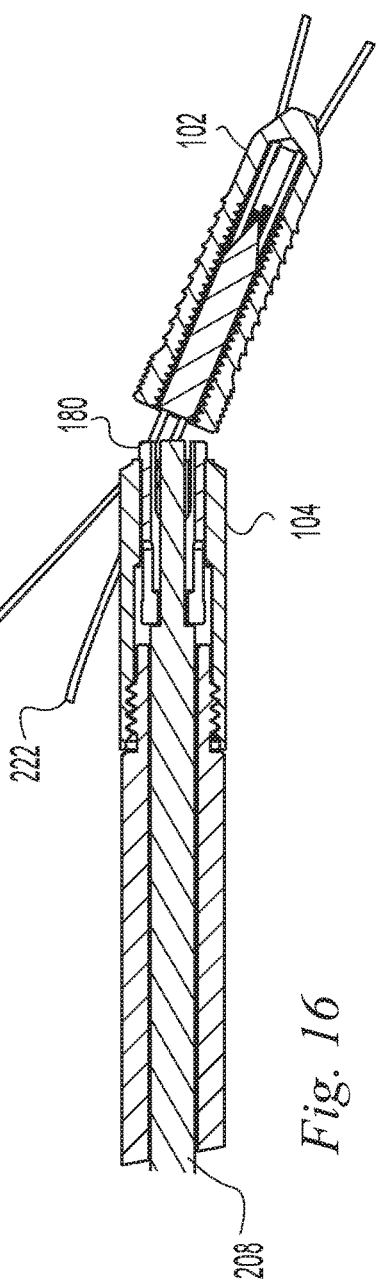

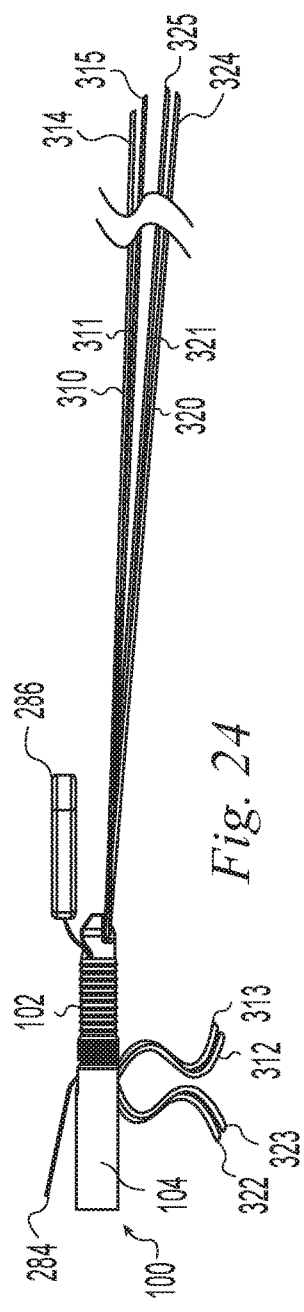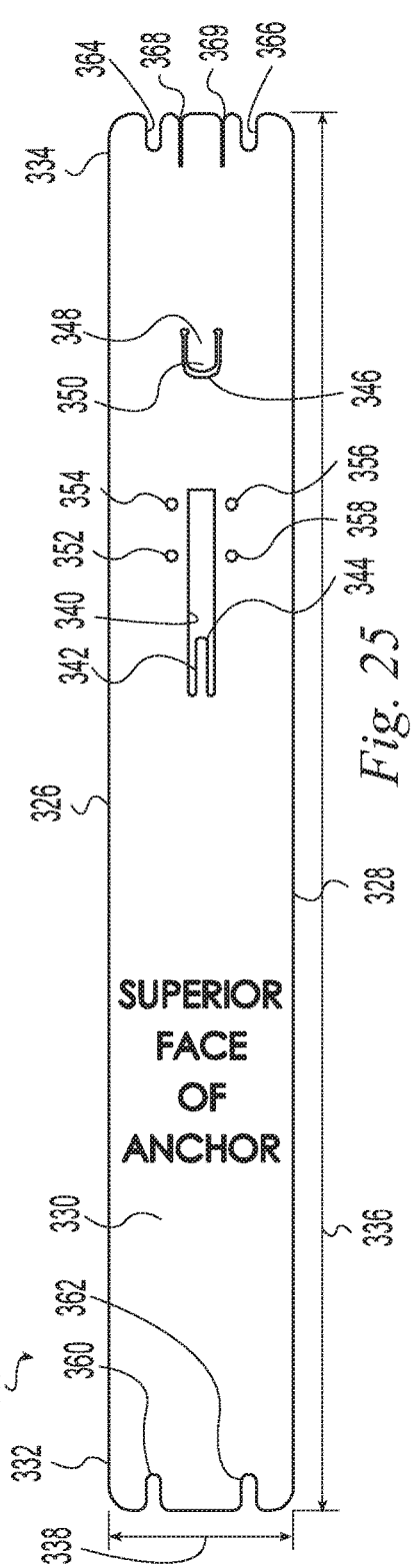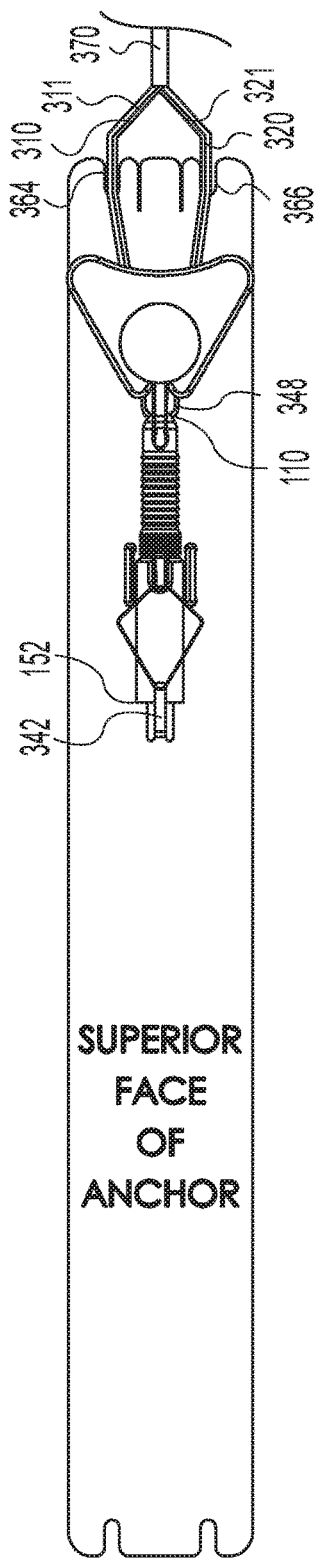
Fig. 24
Fig. 25
Fig. 26

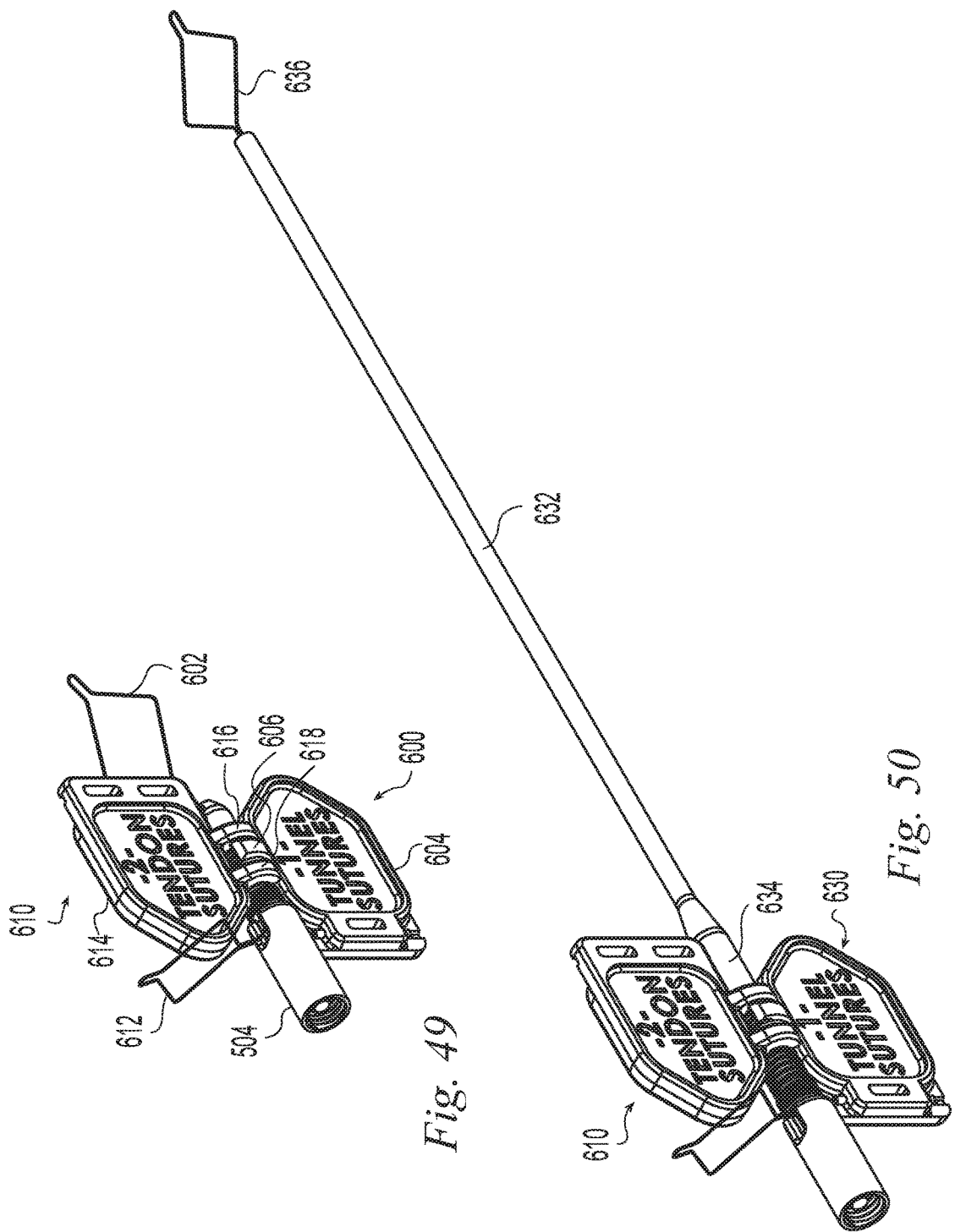

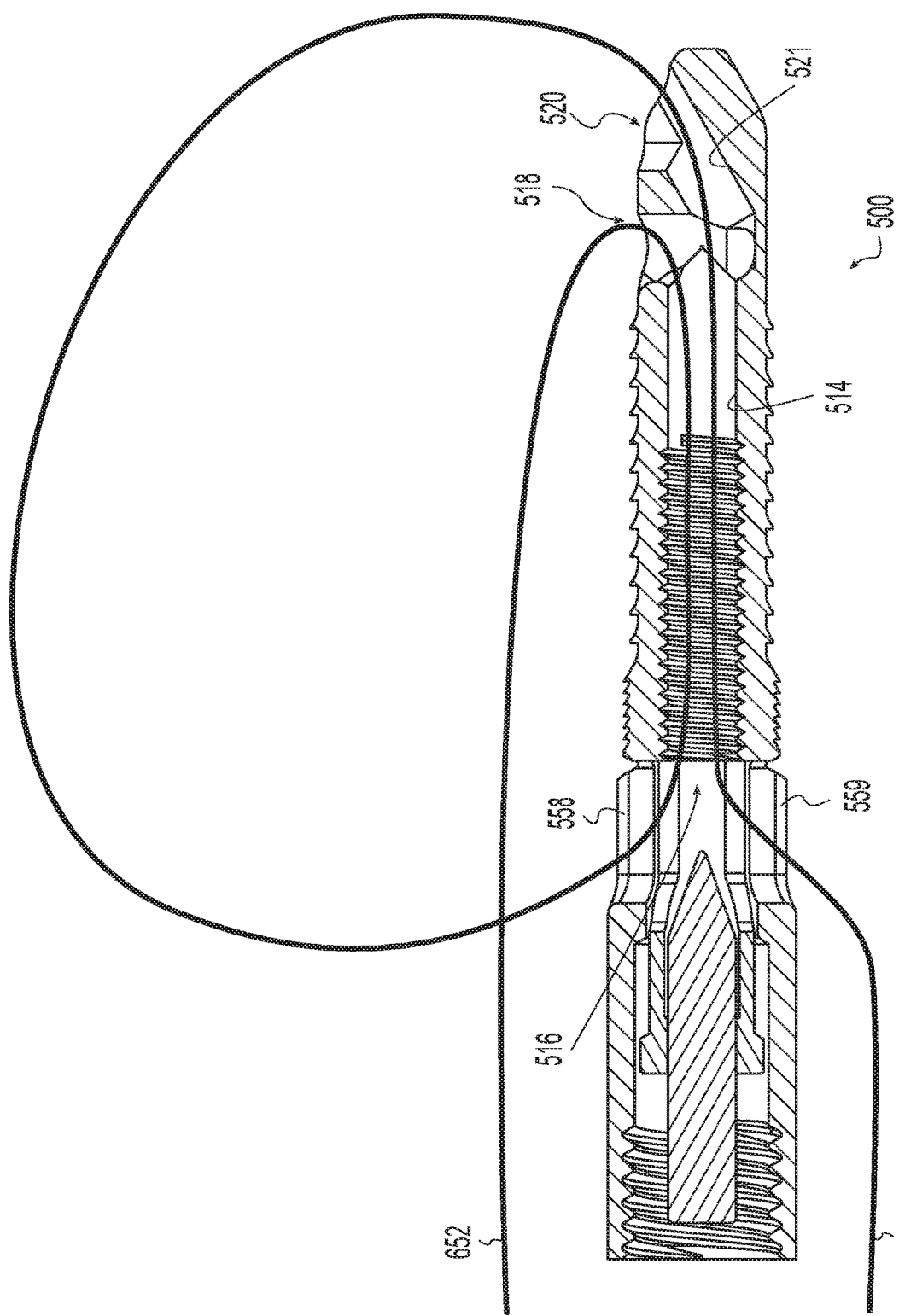

TRANSOSSEOUS SUTURE ANCHOR METHOD

CROSS-REFERENCE TO RELATED APPLICATIONS

This application claims the benefit of U.S. Provisional Application No. 62/200,696, filed Aug. 4, 2015, which is hereby incorporated by reference.

FIELD OF THE INVENTION

Examples of the invention relate to implants, instruments, and methods for surgical transosseous attachment to a bone. More particularly, examples of the invention relate to knotless suture anchors.

BACKGROUND

A variety of surgical procedures require the attachment of something relative to a surgical site. For example, in surgery relating to the skeletal system, it is often advantageous to attach soft tissue, suture, implants, and/or other items in or adjacent to a bone. For example, soft tissues such as ligaments, tendons, fascia, other capsular material, and/or muscle may be attached to a bone. Such soft tissues may be adjacent bones at skeletal joints including but not limited to the joints of the hands and feet, ankle, wrist, knee, elbow, hip, shoulder, and spine. For example, it is often advantageous to pass a suture through a portion of a bone to form a transosseous attachment to the bone.

SUMMARY

Examples of the invention include implants, instruments, and methods for surgical transosseous attachment to a bone. More particularly, examples of the invention relate to knotless suture anchors.

In an example of the invention, a method of attaching a suture to a bone includes passing a portion of a suture through a bone so that a first portion of the suture extends from a first opening in the bone and a second portion of the suture extends from a second opening in the bone; passing the second portion of the suture through a portion of a suture anchor body in a proximal to distal direction, the suture anchor body having a proximal end and a distal end; passing the second portion of the suture alongside an outer surface of the suture anchor body in a distal to proximal direction; and then inserting the suture anchor into the bone through one of the first and second openings, the distal end being inserted first through the opening.

In an example of the invention, a method of attaching a suture to a bone includes disengaging a first portion of a suture extending from a distal end of a suture anchor from a suture keeper, a second portion of the suture extending from a proximal end of the suture anchor being joined to the suture keeper; then passing the first suture portion through a patient's body tissue; then inserting the suture anchor body into a hole in a bone; and then separating the suture keeper from the second portion of the suture.

In an example of the invention, a method of attaching a suture to a bone includes passing a first portion of a suture through a bone; passing the first portion through a soft tissue; passing the first portion outside of a patient's body; tying a knot in the first portion; pulling a second portion of the suture joined to the first portion to move the knot into the patient to a position adjacent to the soft tissue; and securing the suture to the bone. In an example of the invention, a method of attaching a suture to a bone includes passing a tube through a portal in a patient's skin, the tube having a suture passing through it; passing the suture through a soft tissue; splitting the tube to free the suture from the tube; and anchoring the suture to a bone.

In an example of the invention, a method of attaching a suture to a bone includes providing a suture anchor having a proximal end, a distal end, a longitudinal passage extending within the suture anchor in a proximal to distal direction, a first opening communicating with the longitudinal passage nearer the proximal end than the distal end, a second opening through the sidewall of the suture anchor nearer the distal end than the proximal end, and a third opening through the sidewall of the suture anchor nearer the distal end than the proximal end, a first suture threader extending within the longitudinal passage between the first and third openings, the first suture threader extending through the first opening to a grip portion outside of the longitudinal passage, the first suture threader extending through the third opening to a suture engaging portion outside of the longitudinal passage, a second suture threader extending within the longitudinal passage between the first and second openings, the second suture threader extending through the first opening to a suture engaging portion outside of the longitudinal passage, the second suture threader extending through the second opening to a grip portion outside of the longitudinal passage; passing a portion of a suture through a bone so that a first portion of the suture extends from a first opening in the bone and a second portion of the suture extends from a second opening in the bone; engaging the first portion of the suture with the first suture passer; pulling on the grip portion of the first suture passer to pass the first portion of the suture through the longitudinal passage in a distal to proximal direction; engaging the second portion of the suture with the second suture passer; pulling on the grip portion of the second suture passer to pass the second portion of the suture through the longitudinal passage in a proximal to distal direction; and then inserting the suture anchor into the bone through one of the first and second openings, the distal end being inserted first through the opening.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 1 is a perspective view of an implant according to an example of the invention;

FIG. 2 is a top view of the implant of FIG. 1;

FIG. 3 is a left side view of the implant of FIG. 1;

FIG. 4 is a front view of the implant of FIG. 1;

FIG. 5 is a right side view of the implant of FIG. 1;

FIG. 6 is a bottom view of the implant of FIG. 1;

FIG. 13 is a side section view of an instrument useable with the implant of FIG. 1 according to an example of the invention;

FIGS. 14-16 are a sequence of detail top section views illustrating the interaction of the implant of FIG. 1 with the instrument of FIG. 13 according to an example of the invention;

FIG. 24 is a side view of the implant of FIG. 1 preloaded with suture and a suture passer according to an example of the invention;

FIG. 25 is a top view of a suture keeper according to an example of the invention;

FIGS. 26-31 are a sequence of top and bottom views of the implant of FIG. 1 preloaded as in FIG. 24 being loaded onto the suture keeper of FIG. 25;

FIG. 49 is a perspective view of the implant of FIG. 42 preloaded with suture passers according to an example of the invention;

FIG. 50 is a perspective view of the implant of FIG. 42 preloaded with suture passers and a suture management tube according to an example of the invention; and FIG. 51 is a side section view of the implant of FIG. 42 with a suture routed according to an example of the invention.

DESCRIPTION OF THE ILLUSTRATIVE EXAMPLES

Figure 7:
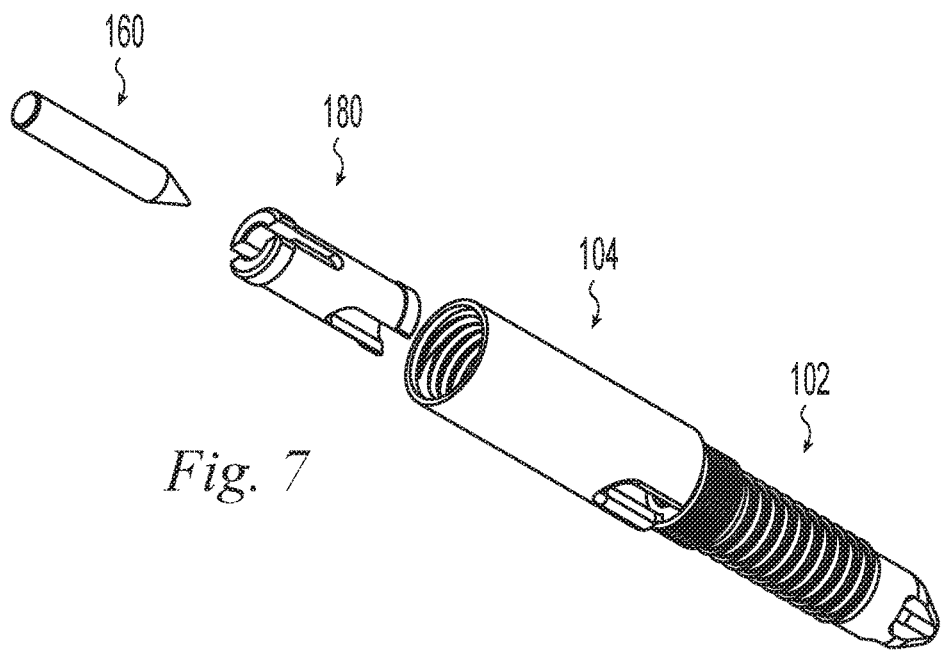
FIG. 7 is an exploded perspective view of the implant of FIG. 1.
Figure 8:
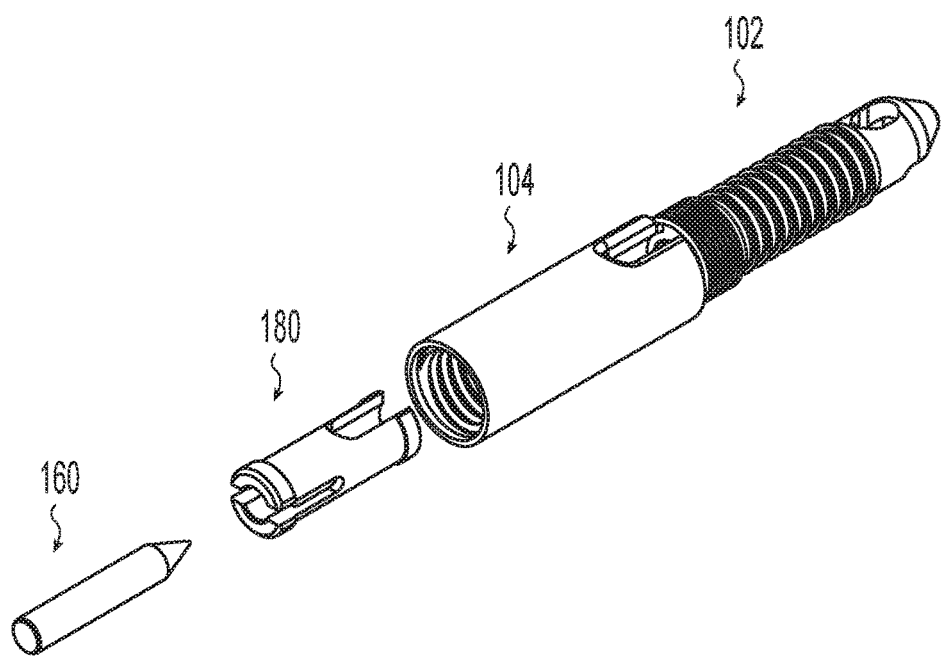
FIG. 8 is an exploded perspective view of the implant of FIG. 1.
Figure 9:
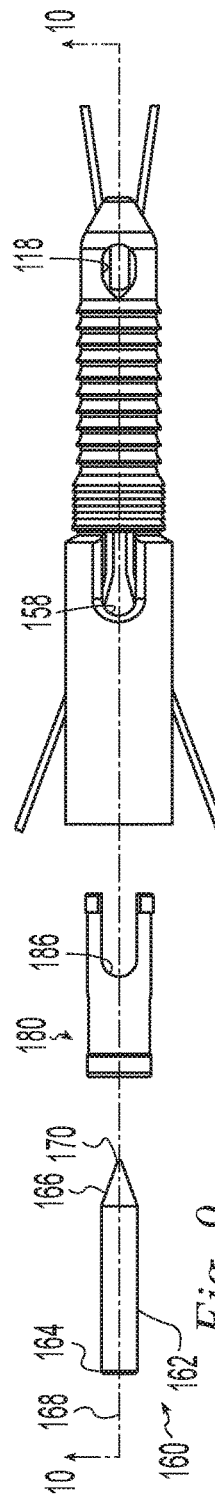
FIG. 9 is an exploded top view of the implant of FIG. 1.
Figure 10:
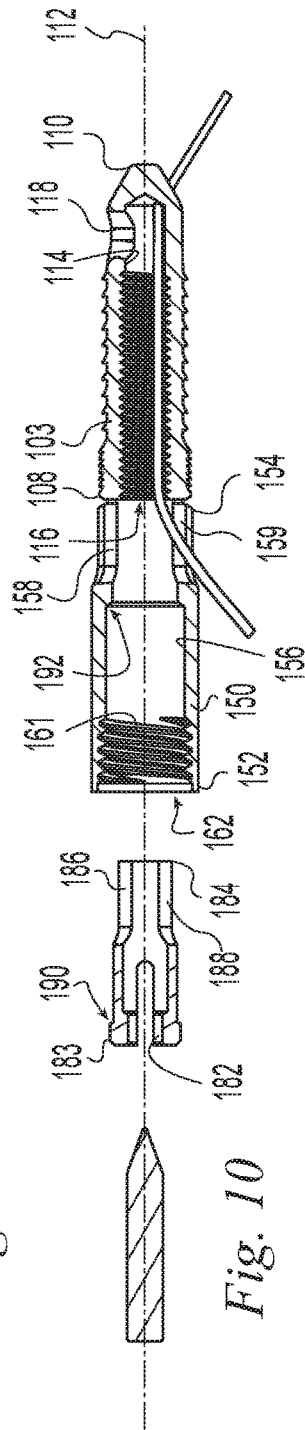
FIG. 10 is an exploded section view taken along line 10-10 of FIG. 9.
Figure 11:
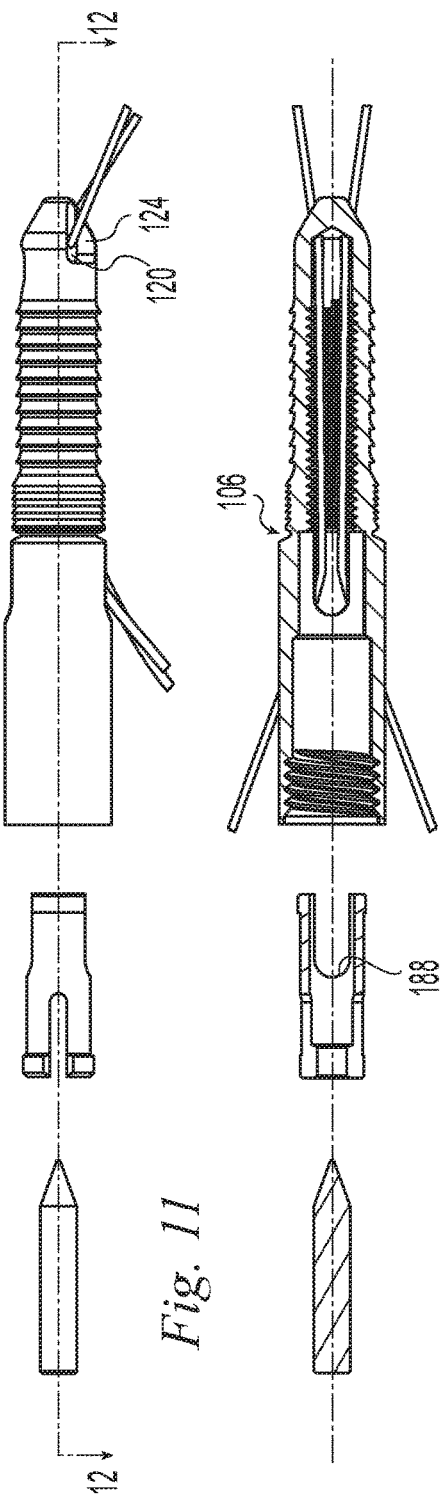
FIG. 11 is an exploded front view of the implant of FIG. 1.
Figure 12:
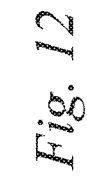
FIG. 12 is an exploded section view taken along line 12-12 of FIG. 11.
Figure 17:
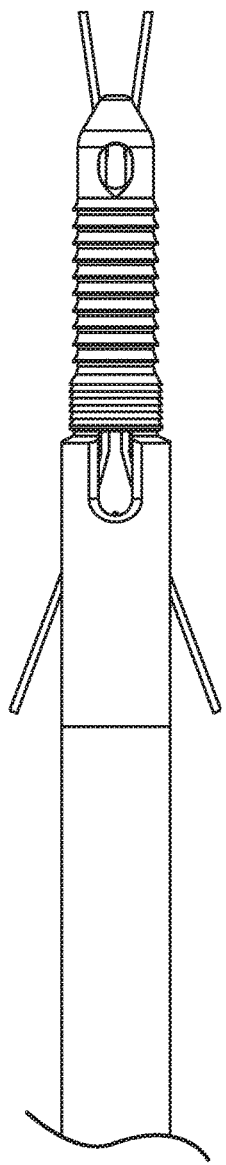
FIGS. 17-19 are a sequence of detail top views illustrating the sequence of FIGS. 14-16.
Figure 18:
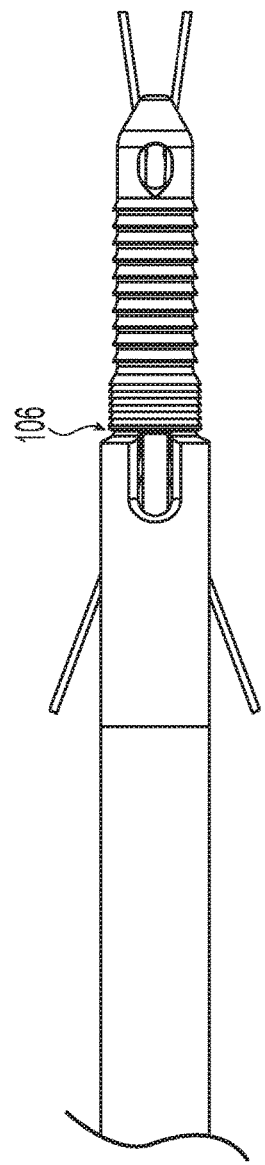
Figure 19:
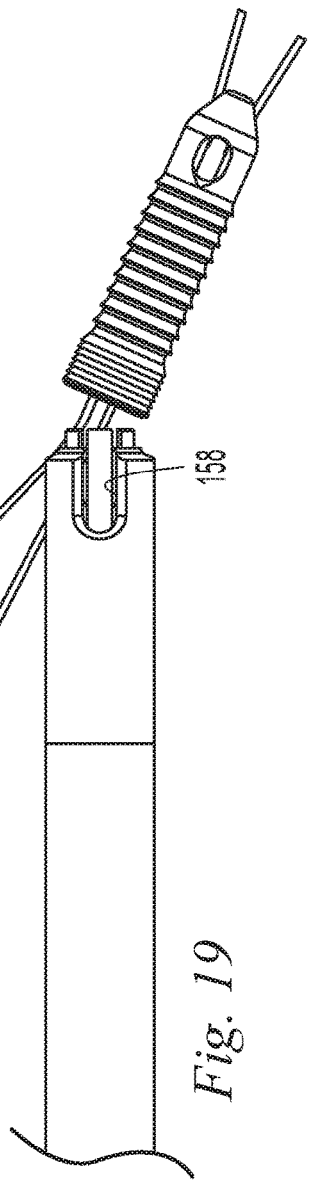

The following illustrative examples depict implants, instruments and methods to anchor a suture to a bone. The illustrative examples depict anchoring a round suture in a bone tunnel to attach soft tissue to the bone. However, examples of instruments and methods of the invention may be used to anchor other elements in a bone tunnel including suture tapes, cables, soft tissues, grafts, and other elements. While illustrative examples of methods depict the attachment of the soft tissue of the rotator cuff to a humeral bone, it will be understood that examples of instruments and methods of the invention may be used to anchor any member in any bone, at surgical sites anywhere in a patient's body, and for any purpose. The terms "suture" and "suture strand" are used herein to mean any strand or flexible member, natural or synthetic, able to be anchored in a bone tunnel and useful in a surgical procedure. The term "transverse" is used herein to mean to cross at an angle; i.e. not parallel. The term includes, but is not limited to right angles.

FIGS. 1-12 depict an illustrative example of a suture anchor. The anchor 100 has an anchor body 102, a proximal member 104 joined to the anchor body 102 by a frangible connection 106 and a suture locking member 160. The frangible connection may include, for example, a thin wall (as shown), a perforated section, an intermediate material such as an adhesive, and/or other suitable frangible constructions. In the illustrative example of FIGS. 1-12, the anchor body 102 is generally cylindrical and has a sidewall 103 (FIG. 10) defining an exterior surface, a proximal end 108, a distal end 110, and a longitudinal axis 112 extending between the proximal and distal ends 108, 110. An interior longitudinal passageway 114 extends at least partway from the proximal end 108 toward the distal end 110. A proximal opening communicates with the longitudinal passageway nearer the proximal end 108 and a distal opening communicates with the longitudinal passageway nearer the distal end 110. In the illustrative embodiment of FIGS. 1-12, the proximal opening 116 communicates through the proximal end 108 of the anchor body 102 along the axis 112 with the passageway 114. The distal opening comprises a plurality of distal openings that communicate from the exterior surface of the anchor body 102 through the sidewall 103 to the passageway 114.

In the illustrative example of FIGS. 1-12, the distal openings include a single superior opening 118 and two inferior openings 120, 122. The superior opening 118 is formed through the sidewall 103 and centered over the longitudinal axis of the anchor body. The two inferior openings 120, 122 are formed through the sidewall 103 opposite the superior opening 118 and spaced on either side of the longitudinal axis and separated by a dividing wall 124. All of the superior and inferior distal openings 118, 120, 122 are spaced proximally away from the distal end 110 of the anchor body.

In the illustrative example of FIGS. 1-12, the anchor body 102 has a first exterior dimension 128, perpendicular to the longitudinal axis, over a first portion 130 of its exterior length 132; a second exterior dimension 134, perpendicular to the longitudinal axis, greater than the first dimension 128, over a second portion 136 of its exterior length 132; and a third exterior dimension 138, perpendicular to the longitudinal axis, greater than the second dimension 134, over a third portion 140 of its exterior length 132. For example, the first dimension 128 may be less than or equal to a radial dimension of a bone hole to ease alignment and initial insertion of the anchor body 102 into the bone hole. The second dimension 134 may be larger than the radial dimension of the bone hole to create a press fit of the second portion 136 within the bone hole to resist removal of the anchor body 102 from the bone hole. The third dimension 138 may create an even tighter press fit in the bone hole. The third portion 140 will require the greatest insertion force. By making the length of the third portion 140 relatively short, the total effort to insert the anchor body 102 will be lessened and the maximum insertion force will only be required to insert the relatively short third portion. The second and third portions 136, 140 may also have ribbed surfaces to further resist removal of the anchor body 102 from the bone hole. The spacing, or pitch, of the ribs may vary. For example, the second portion 136 may have ribs with relatively wider spacing for positioning in a relatively wide band of cancellous bone and the third portion 140 may have ribs with relatively narrower spacing for positioning in a relatively narrow band of cortical bone.

In the illustrative example of FIGS. 1-12, the proximal member 104 is generally cylindrical and has a sidewall 150

(FIG. 10) defining an exterior surface, a proximal end 152, a distal end 154, and a longitudinal axis coaxial with the anchor body longitudinal axis 112 extending between the proximal and distal ends 152, 154. An axial through bore 156 extends through the proximal member 104 from the proximal end 152 to the distal end 154 and communicates with the longitudinal passageway 114 of the anchor body 102. At least one opening formed through the sidewall 150 of the proximal member 104 allows one or more sutures to be routed through the anchor body 102 without passing through the proximal end of the proximal member axial through bore 156. In the illustrative example of FIGS. 1-12, a first, superior "U"-shaped opening 158 is formed through the sidewall 150 near the distal end 154 and a second, inferior "U"-shaped opening 159 is formed through the sidewall 150 near the distal end 154 opposite the first opening 158. The "U"-shaped openings intersect the frangible connection 106. While the proximal member 104 and anchor body 102 are joined, the "U"-shaped openings 158, 159 each have a closed perimeter. When the proximal member 104 and anchor body 102 are separated at the frangible connection 106, the distal perimeter of each opening 158, 159 is removed such that separation of the proximal member 104 and anchor body 102 at the frangible connection 106 transforms the opening 158, 159 into open, "U"-shaped slots with the open side facing distally. The proximal member 104 includes an engagement portion for engaging a driver. In the illustrative example of FIGS. 1-12, the engagement portion includes an internal helical thread 161 operable to engage a driver in axial force transmitting relationship.

In the illustrative example of FIGS. 1-12, the suture locking member 160 is in the form of an interference member operable to axially slide into the longitudinal passageway 114 of the anchor body 102 to secure a suture within the longitudinal passageway 114 by compressing the suture between the locking member 160 and the anchor body 102. In the illustrative example of FIGS. 1-12, the suture locking member 160 has an elongate cylindrical body 162 having a proximal end 164, a distal end 166, and a longitudinal axis 168 extending between the proximal and distal ends 164, 166. The body 162 has a dimension perpendicular to the longitudinal axis 168 less than or equal to the diameter of the anchor body passageway 114. Preferably the body 162 tapers distally. More preferably the body 162 tapers to a point 170.

In the illustrative example of FIGS. 1-12, the suture locking member 160 is mounted in the axial through bore 156 of the proximal member 104 in axial sliding relationship so that it may be pressed out of the proximal member 104 and into the anchor body 102 to lock a suture in the anchor body 102.

In the illustrative example of FIGS. 1-12, the suture locking member 160 is retained in the proximal member 104 by a retainer 180 having an outer surface engaging the axial through bore 156 of the proximal member in axial sliding relationship and an axial aperture 182 receiving the locking member 160 in axial sliding relationship. The retainer 180 is also arranged to engage the anchor body 102 in axial force transmitting relationship. In the illustrative example of FIGS. 1-12, the retainer 180 is generally cylindrical and the axial aperture 182 extends through the retainer 180 from a proximal end 183 to a distal end 184. The outer diameter of the distal end 184 of the retainer 180 is larger than the diameter of the passageway 114 in the implant body 102. The distal end of the retainer 180 is operable to engage the proximal end of the implant body 102. The retainer 180 includes opposed superior and inferior "U"-shaped slots 186, 188 opening distally and aligning with the superior and inferior "U"-shaped openings 158, 159 in the proximal member 104 when the retainer 180 is seated in the proximal member 104. The retainer 180 includes a distal facing shoulder 190 operable to engage a proximal facing shoulder 192 formed in the through bore 156 of the proximal member to prevent the retainer from being completely expelled distally from the proximal member 104.

FIG. 13 depicts an illustrative example of an inserter 200 for use with the suture anchor 100. FIGS. 14-19 depict the inserter 200 in use with the suture anchor 100. The inserter 200 extends from a proximal end 202 to a distal end 204. The inserter 200 has an elongated hollow shaft 206 and an elongated pushrod 208 mounted for axial translation within the hollow shaft. The shaft 206 includes an engagement feature at its distal end operable to engage the proximal member 104 of the suture anchor 100 in axial force transmitting relationship. In the illustrative example of FIG. 13, the shaft 206 includes an external helical thread 216 engageable with the internal helical thread 161 of the proximal member 104 (FIG. 14). The distal end of the pushrod 208 has a first portion 210 sized to engage the proximal end of the suture locking member 160 in axial force transmitting relationship while being operable to slide through the aperture 182 of the retainer 180. The distal end of the pushrod 208 has a second portion 212 sized to engage the proximal end of the retainer 180 in axial force transmitting relationship. The first portion 210 extends distally from the second portion 212. An advancement mechanism 214 at the proximal end of the inserter 200 is operable to advance the pushrod 208 distally relative to the shaft 206. For example, the advancement mechanism 214 may include any pushrod advancement mechanism such as those well known in the art for advancing plungers in syringe injectors, bone cement injectors, and other liquid and paste dispensers. The example of FIG. 13 illustrates such a mechanism including a trigger mounted to a base member in pivoting relationship. The pushrod is slidingly engaged with the base member and a pair of advancement plates. When the trigger is actuated, it presses on the advancement plates causing them to tilt and bind on the pushrod. Further actuation of the trigger advances the advancement plates and the pushrod distally together. When the trigger is released, a spring straightens the advancement plates and moves the advancement plates and the trigger proximally back to their initial positions. A ratchet mechanism prevents the pushrod from moving proximally. The ratchet mechanism includes ratchet teeth cut into the proximal end of the pushrod and a spring loaded ratchet pawl mounted in the base member at the rear of the pushrod. An actuator (not shown) may be actuated to disengage the ratchet pawl so that the pushrod may be moved proximally and reset to its initial position.

Referring to FIGS. 14-19 one or more sutures are threaded through the anchor body 102 between the proximal and distal openings. In the illustrative example of FIGS. 14-19, separate suture limbs 220, 222 are threaded through each of the inferior distal openings 120, 122 of the anchor body 102, through the longitudinal passageway 114 of the anchor body 102, out the proximal opening 116 of the anchor body 102 and down through the inferior "U"-shaped slot 188 of the retainer 180 and the inferior "U"-shaped opening 159 of the proximal member 104. The suture locking member 160 is retained within the retainer 180 which is received in the proximal member 104. The shaft 206 of the inserter 200 is threadingly engaged with the proximal end of the proximal member 104.

In FIG. 15, the advancement mechanism 214 has been operated to advance the pushrod 208 so that it has pushed the suture locking member 160 out of the proximal member 104 and into the anchor body 102 to secure the suture limbs 220, 222 within the anchor body 102. Preferably, the first portion 210 of the pushrod 208 extends sufficiently far distally from the second portion 212 of the pushrod 208 that the suture locking member is fully inserted into the anchor body 102 before the second portion 212 of the pushrod begins to transmit axial force through the retainer 180 to the proximal end 108 of the anchor body 102. Once the suture locking member is fully inserted, further operation of the advancement mechanism 214 presses the second portion 212 of the pushrod against the retainer 180 which presses against the anchor body 102 causing it to separate from the proximal member 104 at the frangible connection 106 as shown in FIG. 16. Separation of the members transforms the "U"-shaped openings 158, 159 of the proximal member 104 into distally open "U"-shaped slots that will release the suture limbs 220, 222 sideways out of the slots without the need for the ends of the suture limbs to be pulled through the openings 158, 159. In this way, the suture limbs 220, 222 will be released from the proximal member 104 even if the ends of the suture limbs 220, 222 are attached at another location or otherwise inaccessible.

Figure 20:
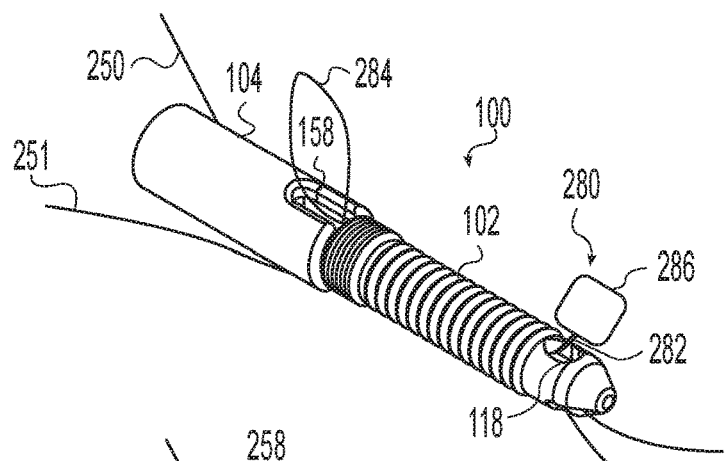
FIGS. 20-22 are a sequence of perspective views illustrating the threading of suture through the implant of FIG. 1 according to an example of the invention.
Figure 21:
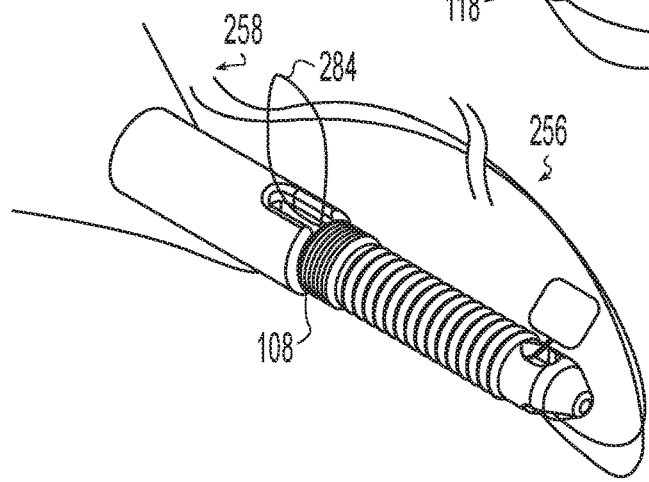
Figure 22:
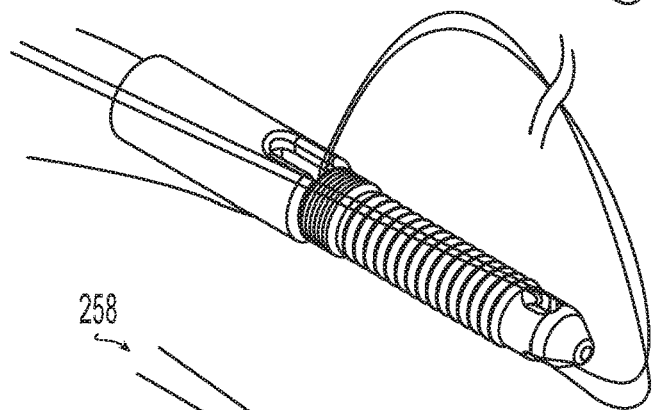
Figure 23:
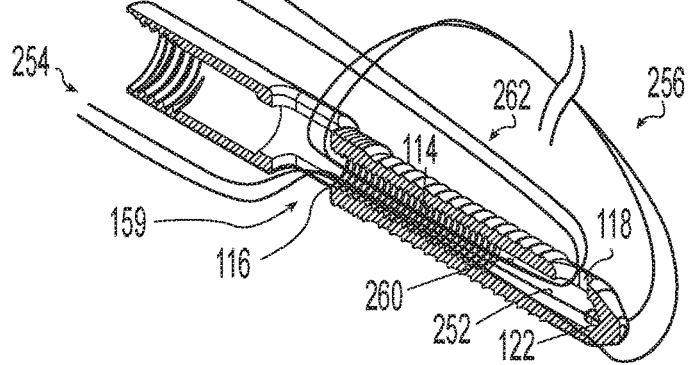
FIG. 23 is a perspective section view illustrating the suture and implant after threading the suture according to the example of FIGS. 20-22.

FIGS. 20-23 depict an illustrative example of a suture routing through the suture anchor 100. A suture threader 280 is pre-loaded into the anchor body 102. The suture threader includes a filament 282 forming a distal loop portion 284 and a proximal grip portion 286 joined to the loop portion. The suture threader 280 is inserted through the longitudinal passageway of the anchor body from the superior distal opening 118 to the proximal opening 116 with at least part of the loop portion 284 extending up and out of the superior "U"-shaped opening 158 of the proximal member 104 and the grip portion 286 extending out of the distal opening 118. In the illustrative example of FIGS. 20-23, two sutures 250, 251 are depicted. Any number of sutures may be utilized in accordance with the invention and each of the depicted sutures may represent multiple sutures that are routed together. For simplicity, the suture locking member 160 and retainer 180 have been omitted from FIGS. 20-23 and the routing of only one 250 of the illustrated sutures will be described in detail. The suture 250 is threaded through an inferior distal opening 122 of the anchor body 102, with a first portion 252 extending through the longitudinal passageway 114 of the anchor body 102 between the proximal opening 116 and the distal opening. A proximal end 254 of the suture 250 extends out the proximal opening 116 of the anchor body 102 and down through the inferior "U"-shaped slot 188 of the retainer 180 (not shown) and the inferior "U"-shaped opening 159 of the proximal member 104. In FIG. 21, a second portion 256 of the suture 250 contiguous to the first portion 252 extends away from the anchor body 102. A distal end 258 of the suture 250 is inserted through the loop portion 284 of the threader 280. The threader 280 is pulled distally through the anchor body 102 to route the distal end 258 of the suture 250 back through the anchor body 102 so that a third portion 260 of the suture contiguous to the second portion 256 extends within the longitudinal passageway 114 between the proximal opening 116 and the superior distal opening 118. The distal end 258 of the suture is then pulled proximally so that a fourth portion 262 of the suture contiguous to the third portion 260 extends along the exterior surface of the anchor body 102 between the distal opening 118 and the proximal end 108. The suture locking member 160 may then be inserted into the anchor body to secure the first portion 252 of the suture and the third portion 260 of the suture within the longitudinal passageway by compressing the suture portions between the suture locking member 160 and the anchor body 102. For example, the suture may be compressed between the sides of the suture locking member and the interior sidewall of the anchor body as shown in FIGS. 15 and 16. In an example according to the invention, the suture 250, 251 and threader may be provided preloaded to the anchor as shown in the configuration of FIG. 20.

FIGS. 24-31 illustrate a suture keeper 300 for managing the suture anchor 100 and sutures in storage and use. Referring to FIG. 24, the suture anchor 100 is prepared as in FIG. 20 with the threader 280 inserted into the suture anchor 100 with the grip portion 286 extending out of the superior distal opening 118 and the loop portion 284 extending out of the superior "U"-shaped opening 158. Four suture strands are loaded in the suture anchor. Preferably each suture strand is uniquely identifiable such as by color, pattern, or otherwise. A first pair of suture strands 310, 311 extends through the longitudinal passageway 114 with proximal ends 312, 313 extending from the inferior "U"-shaped opening 159 and distal ends 314, 315 extending from the first inferior distal opening 120. A second pair of suture strands 320, 321 extends through the longitudinal passageway 114 with proximal ends 322, 323 extending from the inferior "U"-shaped opening 159 and distal ends 324, 325 extending from the second inferior distal opening 122.

Referring to FIG. 25, the suture keeper 300 includes an elongate, generally planar body 330 extending from a proximal end 332 to a distal end 334 and having a length 336 between the proximal and distal ends 332, 334 and a width 338 between first and second sides 326, 328. A first slot 340 formed in the body 330 defines a first, proximal, cantilevered tab 342 free at its distal end 344. Preferably the first slot 340 is narrower than the suture anchor 100 so that the suture anchor can lie in the first slot 340 without passing through the first slot 340. A second slot 346 defines a second, distal, cantilevered tab 348 free at its proximal end 350. Four holes are formed through the body 330 adjacent the first slot 340 with a first pair of holes 352, 354 adjacent a side of the first slot 340 nearer the first side 326 of the body 330 and a second pair of holes 356, 358 adjacent an opposite side of the first slot 340 nearer the second side 328 of the body 330. First and second spaced apart proximal notches 360, 362 are formed into the proximal end 332 of the body 330 with the notches 360, 362 being nearer the first and second sides 326, 328 of the body 330 respectively. First and second spaced apart distal notches 364, 366 are formed into the distal end 334 of the body 330 with the notches 364, 366 being nearer the first and second sides 326, 328 of the body respectively. First and second spaced apart distal slits 368, 369 are formed in the distal end 334 of the body 330 with the slits 368, 369 being nearer the first and second sides 326, 328 of the body respectively. Preferably the distal slits 368, 369 are located between the distal notches 364, 366. In the illustrative example of FIG. 25, the suture keeper is made from a thin, flexible sheet of material.

Figure 27:
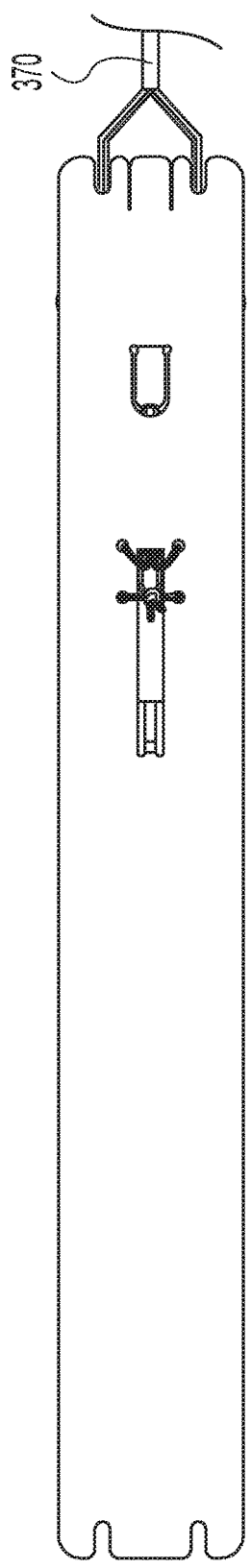

Referring to FIG. 26, a tube 370 is placed over the distal ends of the suture strands of the suture anchor 100 of FIG. 24. Optionally, the tube may be a dual lumen tube so that each pair of suture strands passes through a separate lumen in the tube further isolating the first and second pairs from one another. Preferably, the tube 370 is frangible so that it may be torn from the sutures. For example, a thin walled tube 370 may be torn along its length to split the tube and remove it laterally away from the sutures. One or more starter notches may be formed in the sidewall at one or both ends to facilitate tearing the tube. The proximal ends 312, 313, 322, 323 of the first and second suture pairs are passed through the first slot 340. The proximal ends 312, 313 of the first suture pair is passed through the distal most hole 354 of the first pair of holes and then through the proximal most hole 352 of the first pair of holes. The proximal ends 322, 323 of the second suture pair is passed through the distal most hole 356 of the second pair of holes and then through the proximal most hole 358 of the second pair of holes. The proximal ends 312, 313, 322, 323 are all tied together to join them to the suture keeper 300 (FIG. 27). Thus joined, the suture keeper prevents the proximal ends from being pulled back into the suture anchor 100. The suture anchor 100 is mounted on the suture keeper 300 by bending the proximal and distal tabs 342, 348 upwardly and inserting the suture anchor 100 into the first slot 340 between the tabs with the proximal tab 342 pressing against the proximal end 152 of the proximal member 104 and the distal tab 348 pressing against the distal end 110 of the anchor body 102 to releasably hold the suture anchor 100. The first pair of suture strands 310, 311 is positioned in the first distal notch 364 and the second pair of suture strands 320, 321 is positioned in the second distal notch 366.

FIG. 27 is a rear view of the configuration of FIG. 26.

Figure 28:
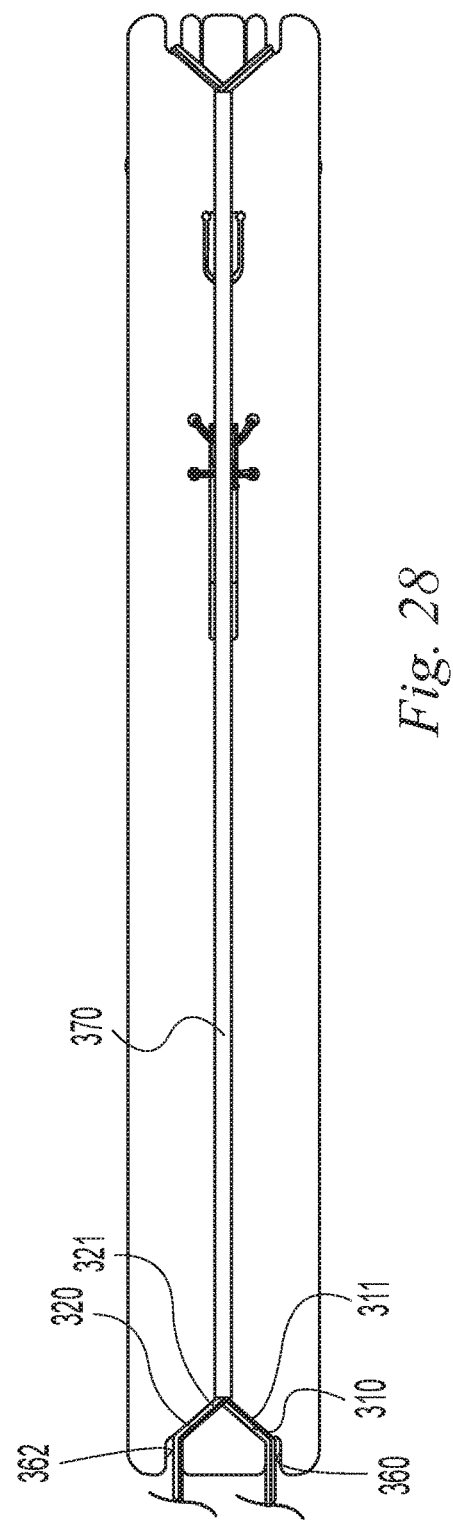

Referring to FIG. 28, the suture strands are folded back through the distal notches so that the suture strands and tube 370 lie along the back of the suture keeper 300. The first pair of suture strands 310, 311 is positioned in the first proximal notch 360 and the second pair of suture strands 320, 321 is positioned in the second proximal notch 362.

Figure 29:
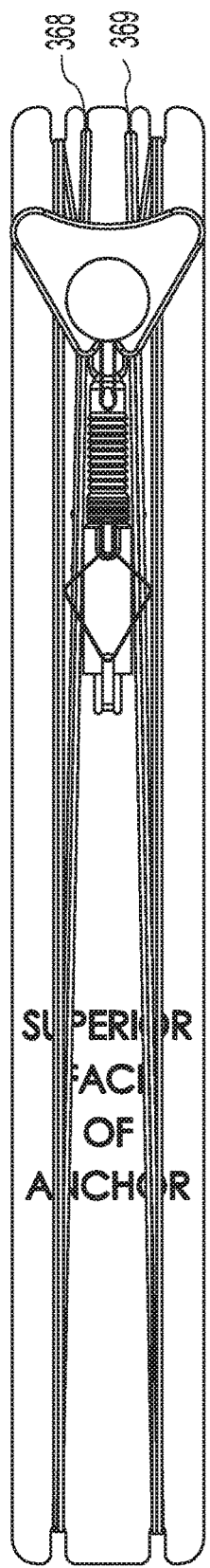

Referring to FIG. 29, the suture strands are wrapped around the suture keeper 300 between the proximal and distal notches as many times as necessary to contain the length of the suture strands while keeping the first pair of strands together on the first side and the second pair of strands together on the second side. The ends of the sutures are pulled into the slits 368, 369 to secure the sutures to the suture keeper 300.

Figure 30:
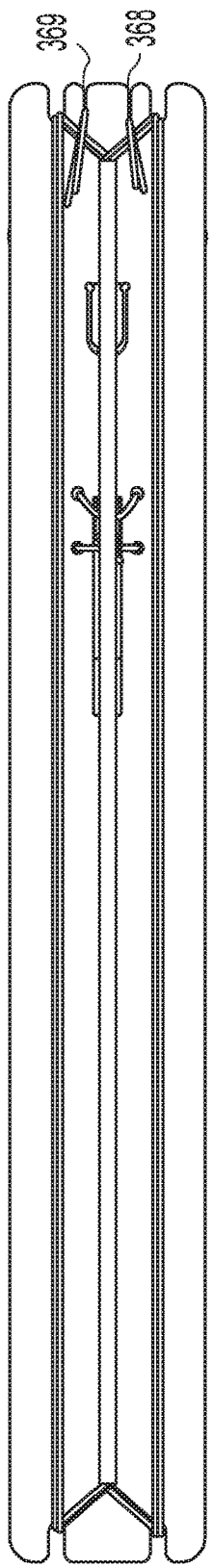

FIG. 30 is a rear view of the configuration of FIG. 29.

Figure 31:
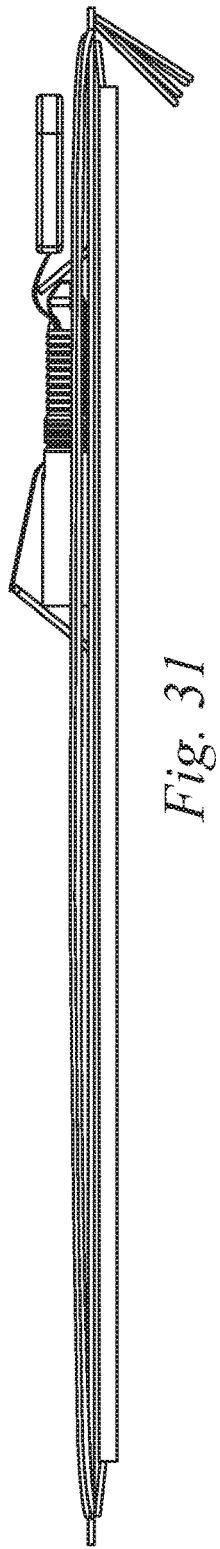

FIG. 31 is a side view of the configuration of FIG. 29.

FIGS. 32-41 illustrate a transosseous surgical repair method using the components illustrated in FIGS. 1-31. The illustrative method of FIGS. 32-41 depicts a rotator cuff repair. However, the implants, instruments, and method illustrated may be used to form transosseous attachments at other locations and for other purposes.

Figure 32:
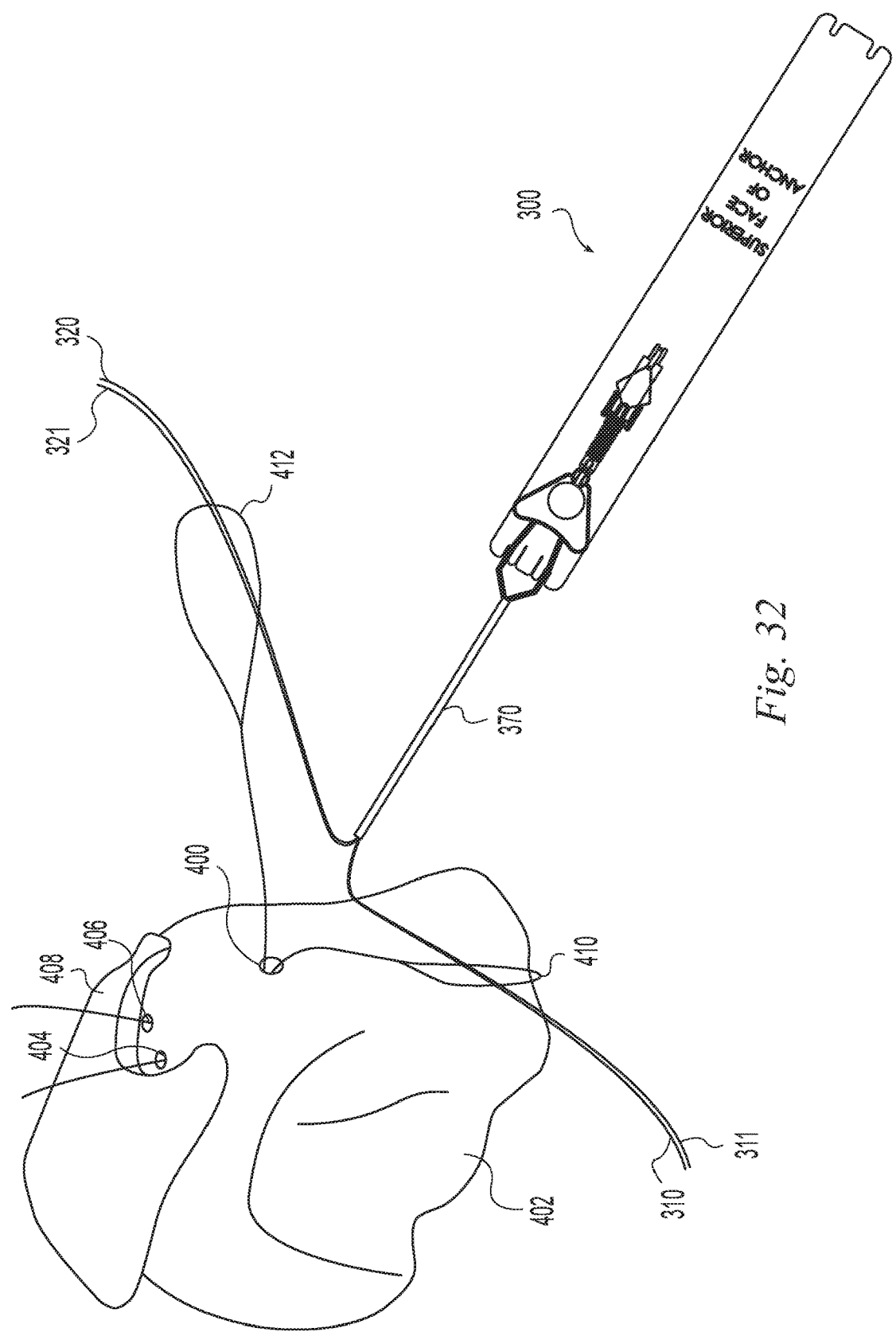
FIGS. 32-41 are a sequence of perspective views illustrating a transosseous surgical repair technique according to an example of the invention.

Referring to FIG. 32, a lateral tunnel 400 has been formed into a humerus 402. First and second medial tunnels 404, 406 have been formed into the humerus 402. The medial tunnels 404, 406 are spaced apart at the surface of the bone near the rotator cuff 408 and the medial tunnels 404, 406 intersect the lateral tunnel 400 inside the humerus 402. First and second suture shuttles 410, 412 are inserted into the medial tunnels 404, 406 and exit the bone through the lateral tunnel 400. The sutures are unwound from the suture keeper and the first pair of suture strands 310, 311 is engaged with the first suture shuttle 410 and the second pair of suture strands 320, 321 is engaged with the second suture shuttle 412. By utilizing the suture keeper 300 to manage the sutures, the various strands of sutures may be easily isolated to prevent tangling and to facilitate independent manipulation of a desired suture strand. The tube 370 may be positioned within a surgical portal (not shown) and acts to confine the suture strands to prevent them from entangling one another and/or instruments and other items passed through the portal.

Figure 33:
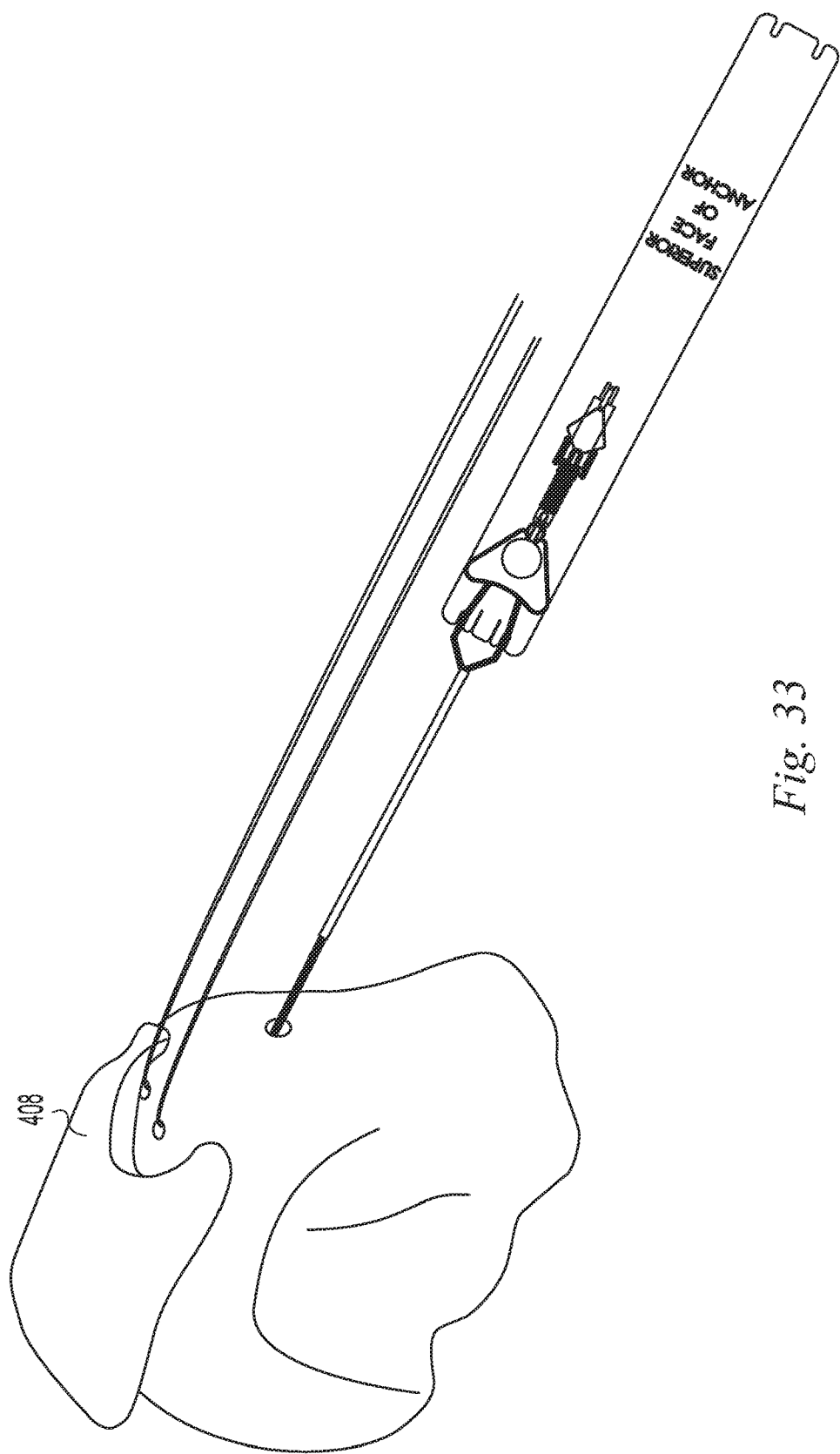

Referring to FIG. 33, the suture shuttles 410, 412 have been pulled to shuttle the suture strands through the bone tunnels.

Figure 34:
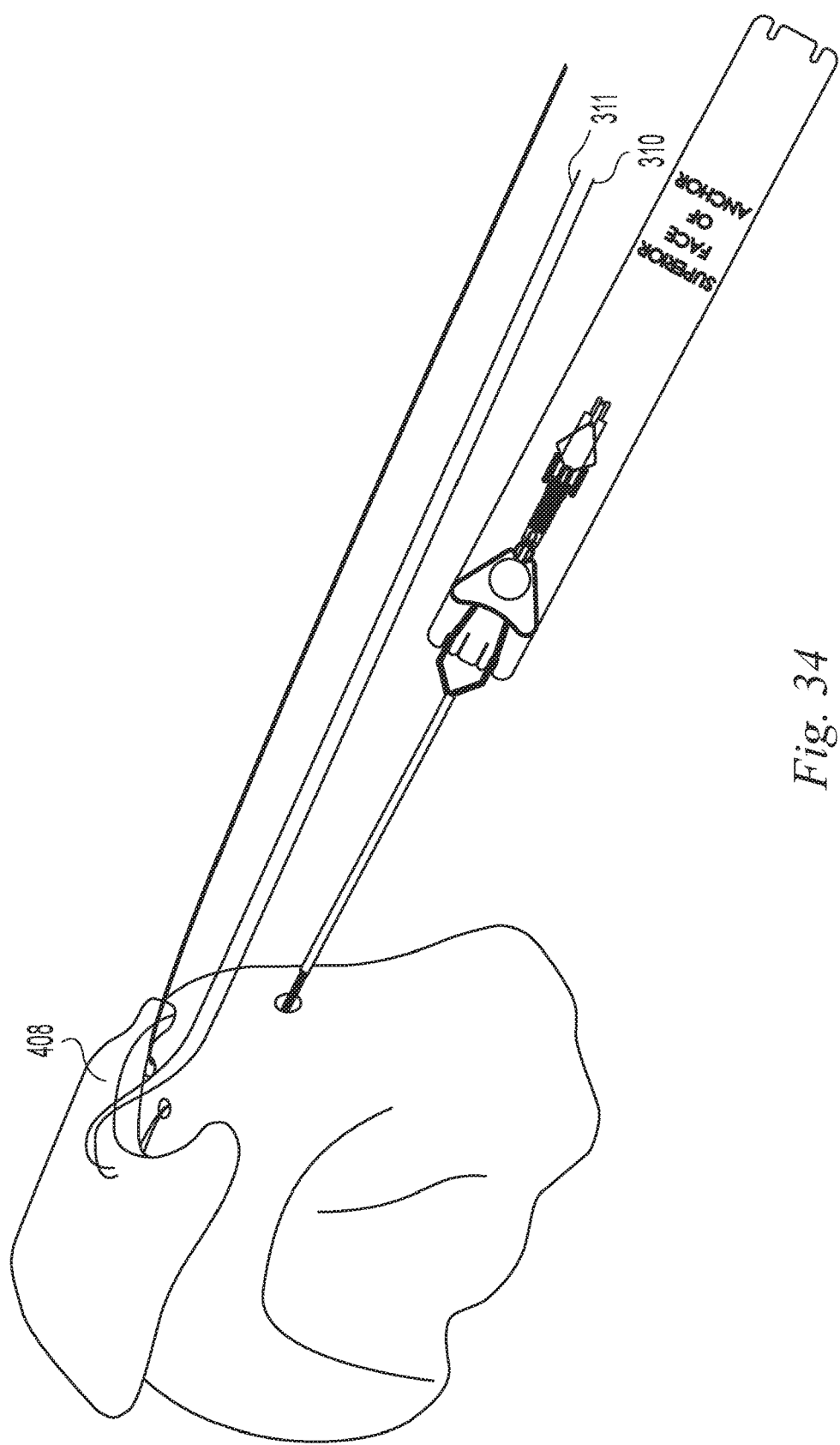

Referring to FIG. 34, the first pair of suture strands 310, 311 has been passed through the rotator cuff 408.

Figure 35:
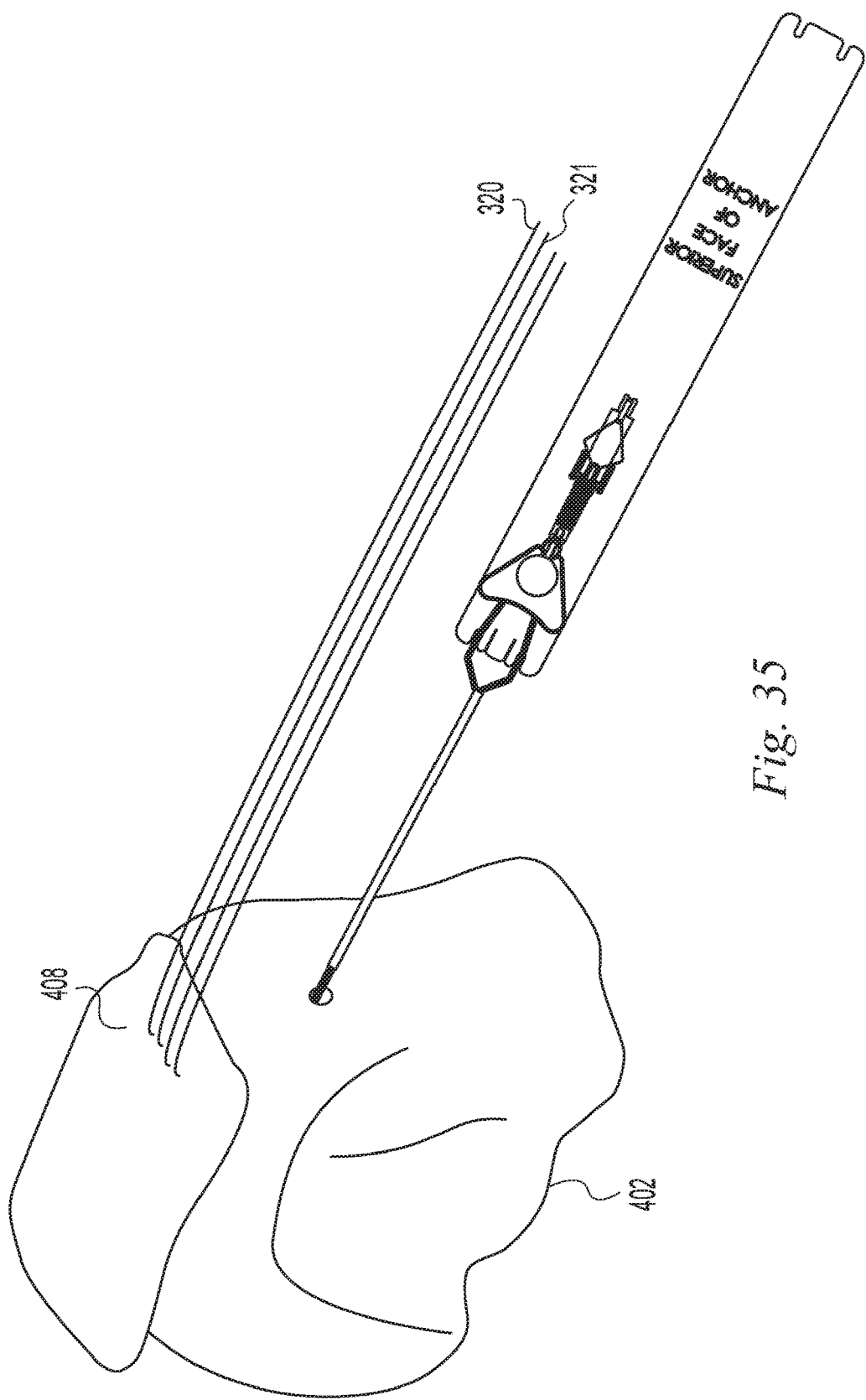

Referring to FIG. 35, the second pair of suture strands 320, 321 has been passed through the rotator cuff 408 and the rotator cuff 408 has been repositioned to a desired lateral margin of the humerus.

Figure 36:
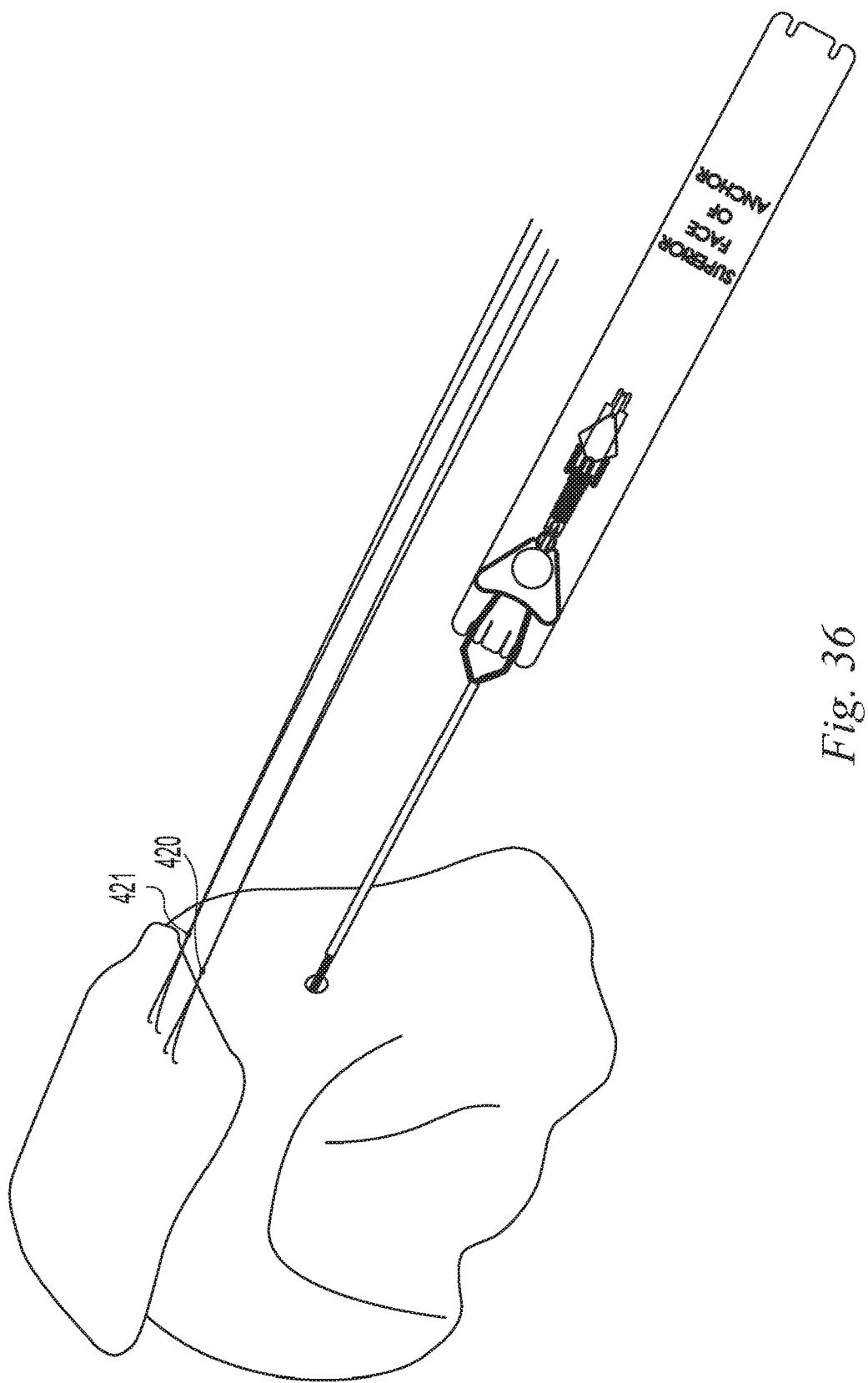

Referring to FIG. 36, a simple overhand knot 420, 421 has been tied in each suture pair. This may be done easily outside the cannula, outside of the patient's body without the need for arthroscopic knot tying techniques.

Figure 37:
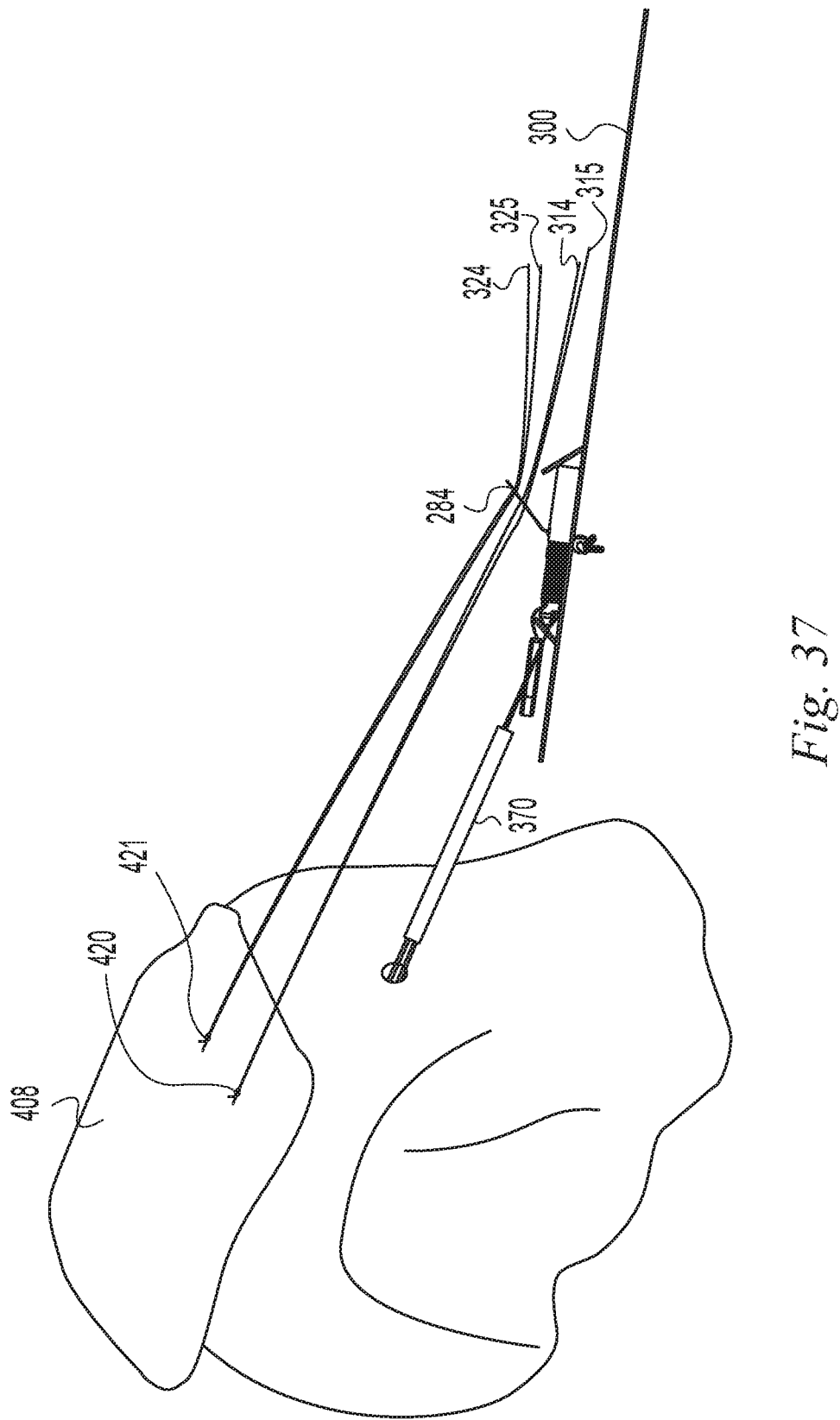

Referring to FIG. 37, the proximal portions of the sutures may be pulled to move the knots 420, 421 into the patient to a position adjacent to the rotator cuff 408. Since the suture strands have been kept separate by the suture keeper 300 and the surgical technique, the knots 420, 421 may be independently positioned and tensioned to provide precise control over the final position and tension of the rotator cuff 408. The distal ends 314, 315, 324, 325 of the suture pairs are passed through the loop 284 of the suture threader 280.

Figure 38:
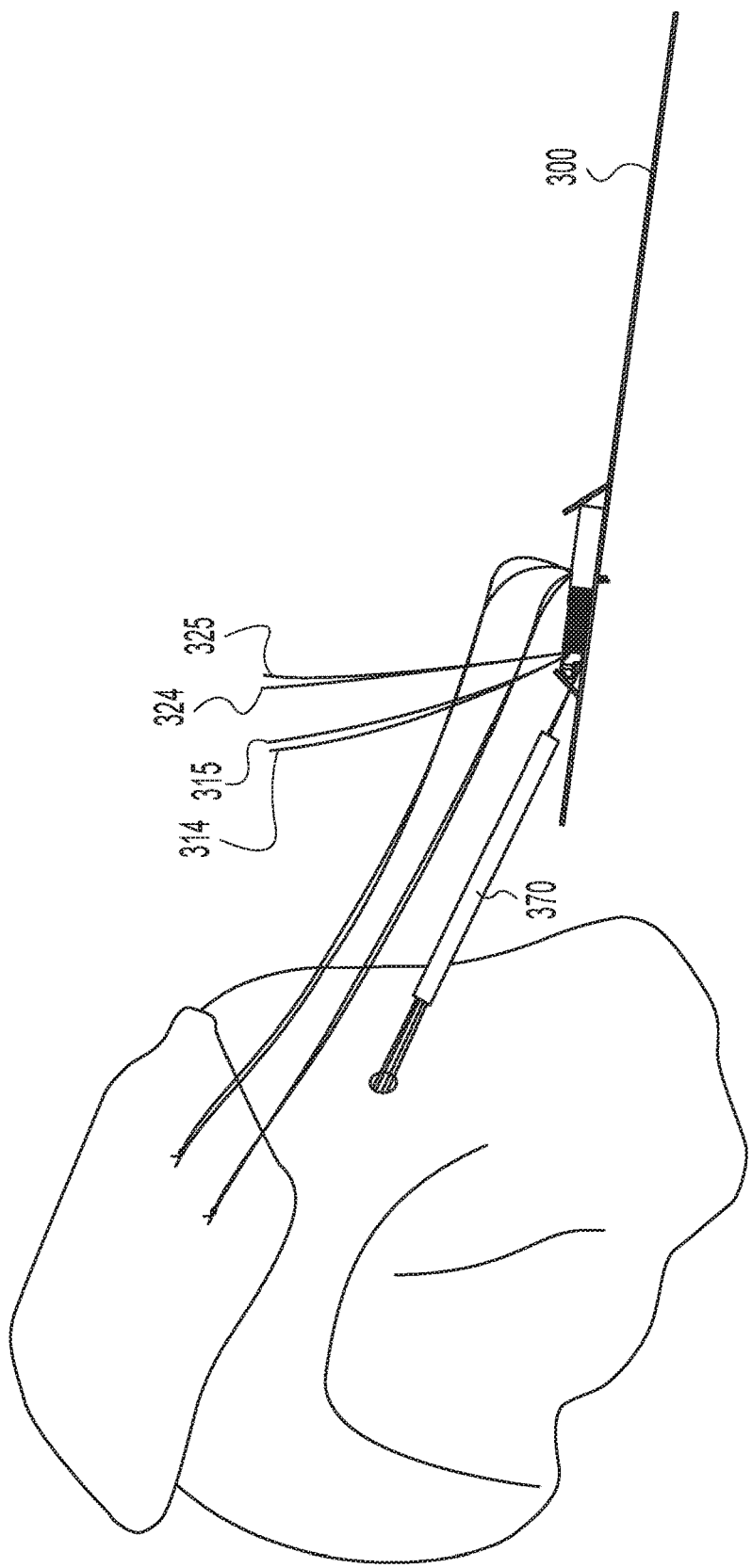

Referring to FIG. 38, the suture threader 280 is pulled out the distal end of the suture anchor 100 to thread the suture strands back through the suture anchor 100 as shown in FIGS. 20-23. The protective tube 370 is split and removed laterally away from the sutures.

Figure 39:
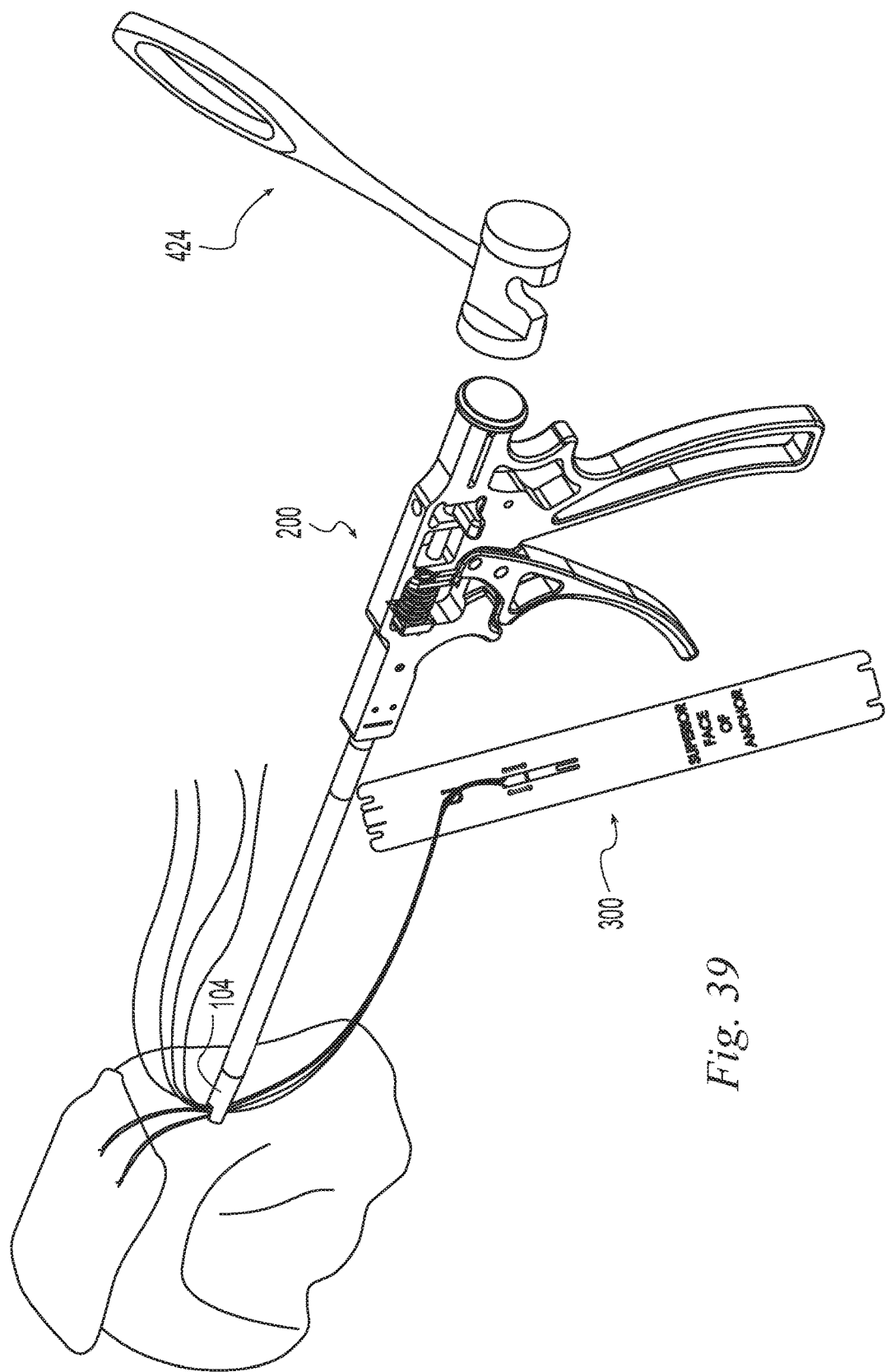

Referring to FIG. 39, the inserter 200 is engaged with the proximal member 104 of the suture anchor 100. Any slack in the suture strands may be pulled through the suture anchor 100 by pulling on the proximal ends of the suture strands retained by the suture keeper 300. The suture anchor 100 is inserted into the lateral bone tunnel 400. A mallet 424 may be used to impact the end of the inserter 200 to urge the suture anchor into the lateral bone tunnel 400.

Figure 40:
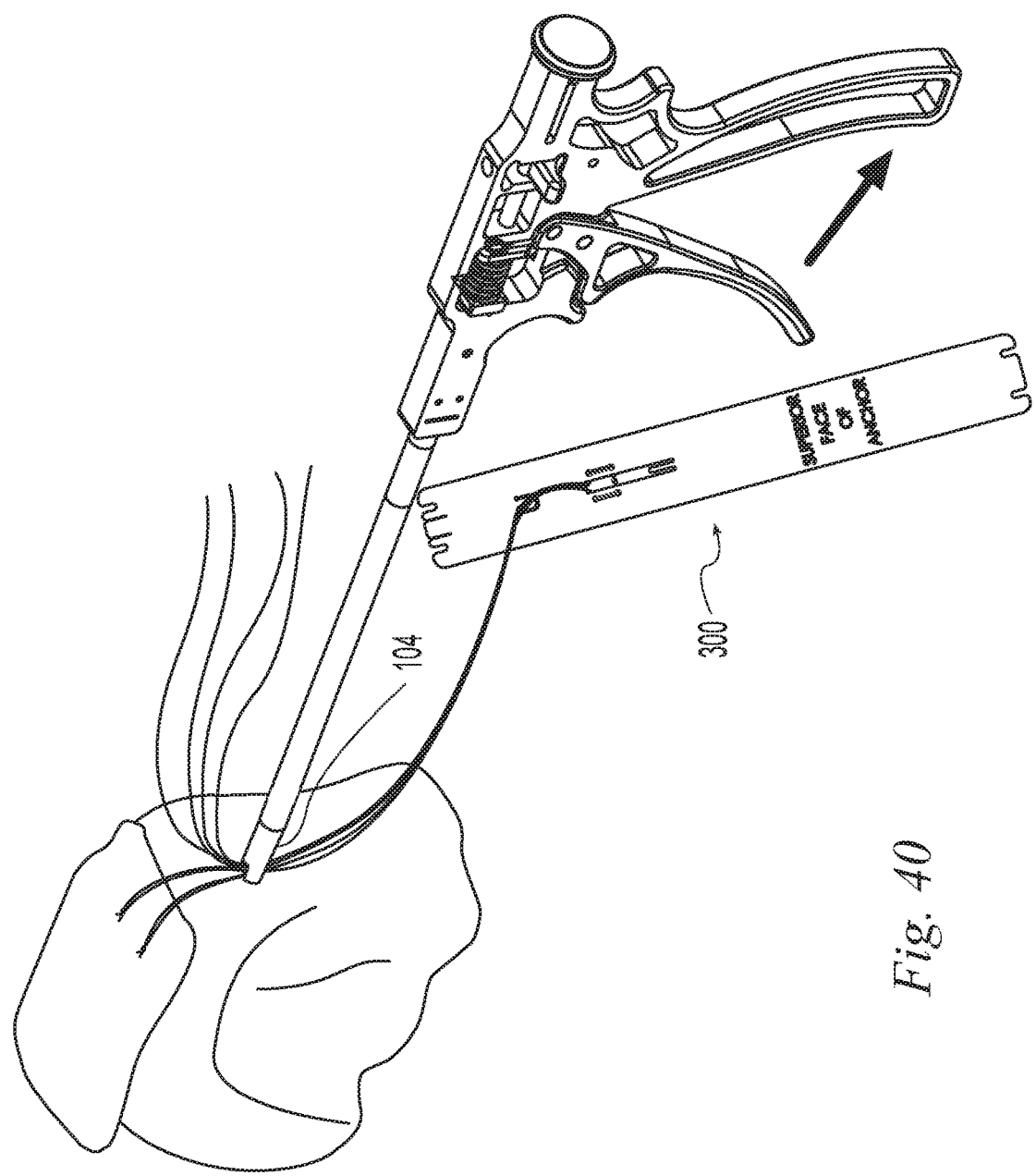

Referring to FIG. 40, the distal portions of the suture strands have passed through the anchor body twice and have been pulled back proximally along the outside of the anchor body so that they are compressed between the anchor body and the bone tunnel wall. The proximal portions of the sutures have passed through the anchor body once, exited outwardly through the inferior distal openings, and then been pulled superiorly through the medial tunnels. This suture routing provides sufficiently low friction that the friction may be overcome by a user to independently pull each suture strand through the anchor body 102 to adjust the position and tension of the soft tissue yet sufficiently high friction that when the suture strands are released the imparted position and tension are maintained so the user can evaluate the repair and determine if further adjustments are needed. The inserter 200 may be used to provide an axial counterforce to keep the anchor body 102 in the bone tunnel while adjustments are made. Once the sutures are adjusted as desired, the inserter 200 is actuated to press the suture locking member 160 into the suture anchor 100 and secure the sutures to the suture anchor 100. The inserter 200 is further actuated to press the retainer 180 against the proximal end of the anchor body 102 and separate the proximal member 104 from the anchor body 102. When the proximal end 104 separates from the anchor body 102, the "U"-shaped openings 158, 159 transform into distally opening slots and the sutures release distally from the slots as the proximal end 104 is pulled away from the bone.

If desired, the proximal ends 312, 313, 322, 323 of the suture strands may be separated from the suture keeper 300, such as by cutting the sutures, and the ends of the sutures may be passed through the soft tissue to form adjunctive stitches to further anchor the soft tissue. The proximal suture ends are preferably used since any loads carried by the proximal suture ends only act perpendicularly on the proximal end of the anchor and thus they do not exert a significant axial force tending to dislodge the anchor body 150 from the lateral tunnel 400.

Figure 41:
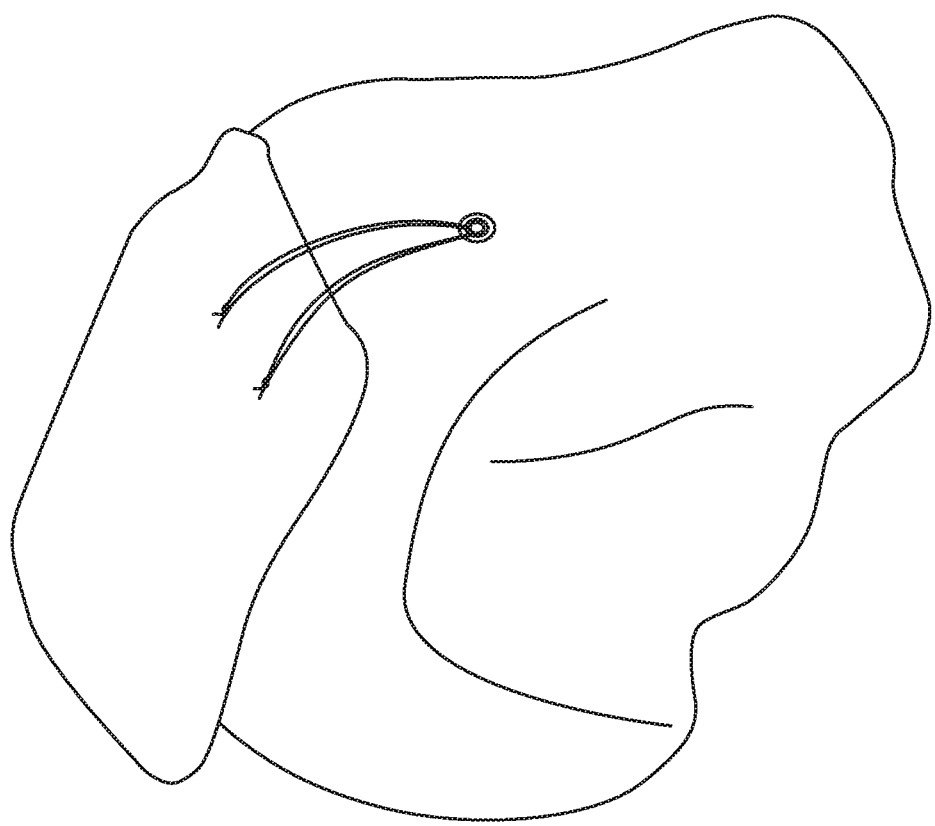
Figure 42:
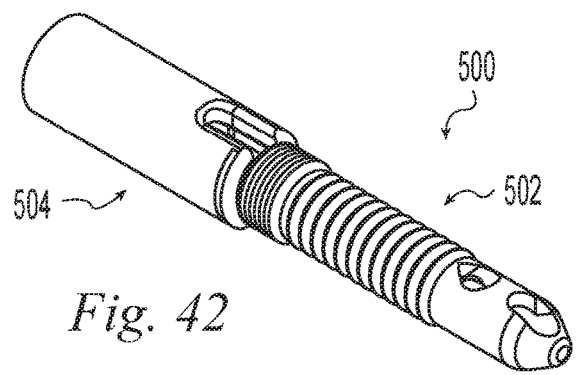
FIG. 42 is a perspective view of an implant according to an example of the invention.
Figure 43:
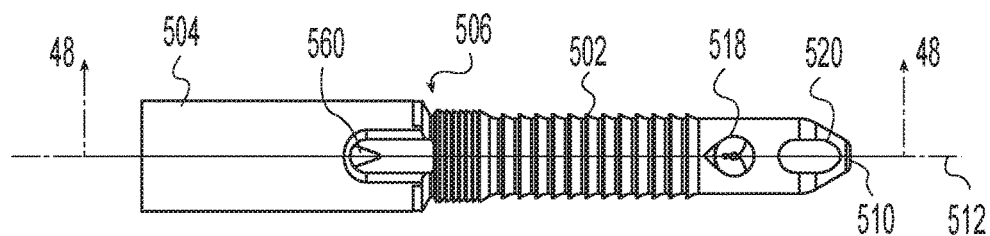
FIG. 43 is a top view of the implant of FIG. 42.
Figure 44:
FIG. 44 is a left side view of the implant of FIG. 42.
Figure 45:
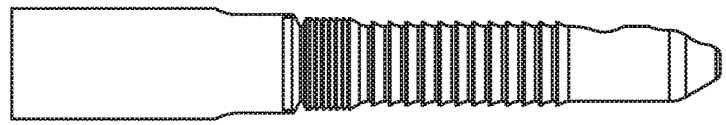
FIG. 45 is a front view of the implant of FIG. 42.
Figure 46:
FIG. 46 is a right side view of the implant of FIG. 42.
Figure 47:
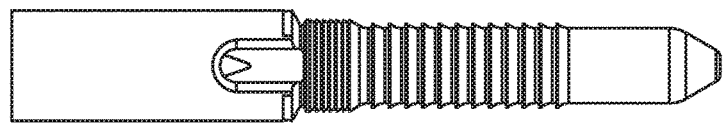
FIG. 47 is a bottom view of the implant of FIG. 42.
Figure 48:
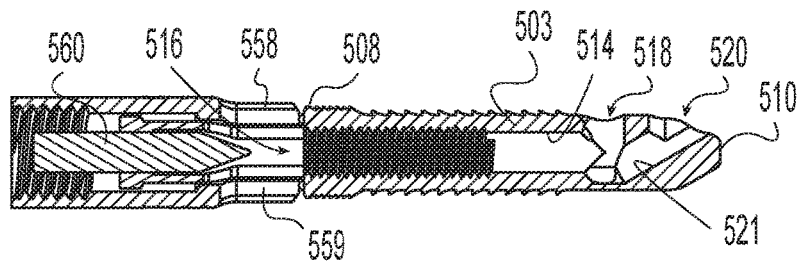
FIG. 48 is a side section view of the implant of FIG. 42 taken along line 48-48 of FIG. 43.

Referring to FIG. 41, any remaining suture ends are trimmed.

FIGS. 42-48 depict a suture anchor 500 according to an example of the invention. The suture anchor 500 is the same as the suture anchor 100 of the example of FIGS. 1-12 except for the configuration of the distal openings. The anchor 500 has an anchor body 502, a proximal member 504 joined to the anchor body 502 by a frangible connection 506 and a suture locking member 560 all configured as in the example of FIGS. 1-12. The anchor body 502 is generally cylindrical and has a sidewall 503 defining an exterior surface, a proximal end 508, a distal end 510, and a longitudinal axis 512 extending between the proximal and distal ends 508, 510. An interior longitudinal passageway 514 extends at least partway from the proximal end 508 toward the distal end 510. A proximal opening 516 communicates through the proximal end 508 of the anchor body 502 along the axis 512 with the interior longitudinal passageway 514. The distal opening comprises a plurality of distal openings that communicate from the exterior surface of the anchor body 502 through the sidewall 503 to the interior longitudinal passageway 514. In the illustrative example of FIGS. 42-48, the distal openings include a first, more proximal superior opening 518 and a second, more distal superior opening 520. The first and second distal openings 518, 520 are formed through the sidewall 503 to communicate with the interior longitudinal passageway 514 and are centered over the longitudinal axis 512 on the same side of the anchor body. The first and second distal openings 518, 520 are spaced proximally away from the distal end 510 of the anchor body. In the example of FIGS. 42-48, the second opening 520 is elongated longitudinally and communicates with a proximally sloping passage 521 that connects it to the interior longitudinal passageway 514.

FIG. 49 depicts the anchor 500 of FIGS. 42-48 preloaded with first and second suture threaders 600, 610. The first threader 600 includes a proximal grip portion 604 and a filament forming a distal loop portion 602 joined to the grip portion. The first threader includes a semi-circular clip 606 sized to snap onto the anchor body to releasably secure the threader to the anchor body. The first suture threader 600 is engaged with the anchor by inserting the distal loop portion 602 through the inferior "U"-shaped opening 559 of the proximal member 504, through the proximal opening 516, along the longitudinal passageway 514, and out through the second superior opening 520. The grip portion is clipped to the anchor body. The second threader 610 includes a proximal grip portion 614 and a filament forming a distal loop portion 612 joined to the grip portion. The second threader includes a pair of semi-circular clips 616, 618 sized to snap onto the anchor body to releasably secure the threader to the anchor body. The second suture threader 602 is engaged with the anchor by inserting the distal loop portion 602 through the first superior opening 518, along the proximally sloping passage 521, along the longitudinal passageway 514, through the proximal opening 516, and out the superior "U"-shaped opening 558 of the proximal member 504. The grip portion is clipped to the anchor body with the second suture threader clips 616, 618 straddling the first suture threader clip 606.

In the example of FIG. 49 the threaders are labeled to facilitate their use in a procedure to attach, for example, a tendon to a bone. The first suture threader 600 is labeled with a "1" and the message "TUNNEL SUTURES" to indicate that it is used, preferably first, to thread sutures extending from the bone tunnel in which the anchor will be seated through the anchor. The second suture threader 610 is labeled with a "2" and the message "TENDON SUTURES" to indicate that it is used, preferably second, to thread sutures extending from the soft tissue, tendon in this example, through the suture anchor.

FIG. 50 also depicts the anchor 500 of FIGS. 42-48 preloaded with first and second suture threaders 630, 610. In this example, the first threader 630 is extended and a tube 632, like the tube 370 of FIG. 26, is placed over the extended portion of the suture threader 630. The tube may, for example, be used to protect, confine, separate, or otherwise aid in suture management as previously described relative to the example of FIG. 26. In the example of FIG. 50, the proximal end of the tube includes an enlarged cylindrical portion 634 that is sized to press over the distal end of the anchor body to releasably join the tube 632 to the anchor. The distal loop portion 636 of the first threader extends out the distal end of the tube 632. As in the example of FIG. 26, the tube 632 is preferably frangible. For example, the tube is preferably longitudinally splittable.

FIGS. 49 and 50 are examples in which a suture anchor is provided for use without any sutures preloaded with the anchor. This provides maximum flexibility to the user to choose the type and number of sutures to be used and also allows for suture manipulation during the surgical procedure without the anchor potentially interfering with certain suture passing techniques. The threaders are pre-loaded to facilitate threading the sutures through the anchor once the sutures are selected and/or positioned in the bone and soft tissue. The configuration of the example of FIG. 49 is compact and may be more suitable for open or shallow minimally invasive surgical procedures. The configuration of the example of FIG. 50 may be more suitable for arthroscopic or otherwise deep surgical procedures in which suture management is more challenging.

FIG. 51 depicts an example of suture routing through the suture anchor 500 of FIGS. 42-48 such as for example using the threaders of FIG. 49 or 50. For example, in a transosseous soft tissue fixation procedure, one or more sutures may be extended through a bone tunnel with a first portion of the suture extending from a first opening of the bone tunnel and a second portion of the suture extending from a second opening of the bone tunnel. For example, in a rotator cuff repair procedure a first portion of suture may extend from a lateral opening of a tunnel formed in a humeral bone and a second portion of suture may extend from a medial opening at a desired attachment location for the soft tissue. The second portion may be passed through soft tissue, for example tissue of the rotator cuff, and extended away from the soft tissue. The suture may be threaded through the anchor 500 using the suture threaders. In an example, the first portion of suture 650 is threaded through the distal loop portion 602 of the first suture threader 600. The grip portion 604 of the first suture threader is grasped and pulled to disengage the clip 606 from the anchor body and pull the first portion of suture 650 through the second superior opening 520 in the suture anchor body, proximally along the longitudinal passageway 514, through the proximal opening 516, and out through the inferior "U"-shaped opening 559. The second portion of suture 652 is threaded through the distal loop portion 612 of the second suture threader 610.

The grip portion 614 of the second suture threader is grasped and pulled to disengage the clips 616, 618 from the anchor body and pull the second portion of suture 652 through the superior "U"-shaped opening 558, through the proximal opening 516, distally along the longitudinal passageway 514, and out through the first superior opening 518.

Specific examples of the invention have been described. However, it will be apparent to one skilled in the art that various changes and substitutions may be made within the scope of the invention defined by the claims. Likewise, it is contemplated, and within the scope of the invention, that the various features of the illustrative examples may be interchanged among the illustrative examples.

The following are further examples of the invention.
1. A knotless suture anchor comprising:
   an anchor body having an exterior surface, a proximal end, a distal end, a longitudinal axis extending between the proximal and distal end, an interior longitudinal passageway extending at least partway from the proximal end toward the distal end, a proximal opening communicating with the longitudinal passageway nearer the proximal end, and a distal opening communicating with the longitudinal passageway nearer the distal end; and
   a first portion of a suture extending within the longitudinal passageway between the proximal opening and the distal opening, a second portion of the suture contiguous to the first portion and extending out of the anchor body, a third portion of the suture contiguous to the second portion and extending within the longitudinal passageway proximally to distally, and a fourth portion of the suture contiguous to the third portion and extending along the exterior surface distally to proximally.
2. The knotless suture anchor of example 1 further comprising an interference member operable to axially slide into the longitudinal passageway and secure the first portion of the suture and the third portion of the suture within the longitudinal passageway by compressing the suture portions between the interference member and the anchor body.
3. The knotless suture anchor of example 1 further comprising a proximal member joined to the anchor body by a frangible connection, a proximal member axial passage within the proximal member, the proximal member axial passage containing an interference member coaxially aligned with the longitudinal passageway.
4. The knotless suture anchor of example 3 further comprising an interference member retainer having a retainer axial passage, the interference member retainer engaging the proximal member axial passage in axial sliding relationship, the interference member engaging the retainer axial passage in axial sliding relationship.
5. The knotless suture anchor of example 4 further comprising an inserter operable to engage the proximal member in axial force transmitting relationship in a first direction, the inserter having a pushrod mounted for axial translation within the inserter, the pushrod being operable to engage the interference member in axial force transmitting relationship in a second direction opposite the first direction and expel the interference member from the proximal member into the anchor body, the pushrod being further operable to engage the interference member retainer in axial force transmitting relationship to press the interference member retainer against the anchor body and separate the anchor body and proximal member at the frangible connection.
6. The knotless suture anchor of example 1 wherein the anchor body has a plurality of distal openings.
7. The knotless suture anchor of example 6 wherein the plurality of distal openings comprises a single opening on a first side of the anchor body and a pair of openings on a second side of the anchor body opposite the first side.
8. The knotless suture anchor of example 6 wherein the plurality of distal openings comprises first and second openings through a sidewall of the anchor body nearer the distal end than the proximal end.
9. The knotless suture anchor of example 6 wherein the first portion of the suture passes through at least one of the plurality of distal openings and the third portion of the suture passes through at least another of the plurality of distal openings.
10. A knotless suture anchor comprising:
    an anchor body having an exterior surface, a proximal end, a distal end, a longitudinal axis extending between the proximal and distal end, an interior longitudinal passageway extending at least partway from the proximal end toward the distal end, a proximal opening communicating with the longitudinal passageway nearer the proximal end, and a first distal opening communicating with the longitudinal passageway nearer the distal end than the proximal end;
    a proximal member joined to the anchor body by a frangible connection, the proximal member having a proximal member axial passage.
11. The knotless suture anchor of example 10 further comprising an interference member held by the proximal member and coaxially aligned with the longitudinal passageway.
12. The knotless suture anchor of example 11 wherein the interference member is mounted in axial sliding relationship within the proximal member and wherein the interference member is operable to slide axially out of the proximal member and into the longitudinal passageway of the anchor body.
13. The knotless suture anchor of example 11 wherein the anchor body further comprises a second distal opening.
14. The knotless suture anchor of example 13 wherein the anchor body further comprises a third distal opening, the first distal opening being on a first side of the anchor body and a the second and third openings being on a second side of the anchor body opposite the first side.
15. The knotless suture anchor of example 13 wherein the first and second distal openings are formed through a sidewall of the anchor body nearer the distal end than the proximal end, the first and second distal openings being aligned on the same side of the anchor body and spaced axially away from one another.
16. The knotless suture anchor of example 13 wherein the first and second distal openings have a continuous strand of suture material passing through them.
17. The knotless suture anchor of example 11 further comprising an interference member retainer having a retainer axial passage, the interference member retainer engaging the proximal member axial passage in axial sliding relationship, the interference member engaging the retainer axial passage in axial sliding relationship.
18. The knotless suture anchor of example 17 further comprising an inserter operable to engage the proximal member in axial force transmitting relationship in a first direction, the inserter having a pushrod mounted for axial translation within the inserter, the pushrod being operable to engage the interference member in axial force transmitting relationship in a second direction opposite the first direction and expel the interference member from the proximal member into the anchor body, the pushrod being further operable to engage the interference member retainer in axial force transmitting relationship to press the interference member retainer against the anchor body and separate the anchor body and proximal member at the frangible connection.

19. The knotless suture anchor of example 10 further comprising a first portion of suture extending within the longitudinal passageway and a second portion of suture contiguous to the first portion of suture extending from the anchor body.

20. The knotless suture anchor of example 19 further comprising a third portion of suture contiguous to the second portion of suture and extending within the longitudinal passageway proximally to distally.

21. The knotless suture anchor of example 20 further comprising a fourth portion of suture contiguous to the third portion and extending along the exterior surface distally to proximally.

22. The knotless suture anchor of example 20 further comprising a second distal opening communicating with the longitudinal passageway nearer the distal end than the proximal end, wherein the first portion of suture passes through one of the first and second distal openings and the third portion of suture passes through the other of the first and second distal openings.

23. The knotless suture anchor of example 19 further comprising a frangible elongate tube having a proximal end and a distal end, wherein the second portion of suture passes through the tube from the proximal end to the distal end.

24. The knotless suture anchor of example 13 further comprising:
   a first suture threader extending within the longitudinal passageway, the first suture threader extending through the proximal opening to a first threader loop end and the first suture threader extending through the first distal opening to a first threader grip end, the first threader loop end defining a suture capture loop; and
   a second suture threader extending within the longitudinal passageway, the second suture threader extending through the proximal opening to a second threader grip end and the second suture threader extending through the second distal opening to a second threader loop end, the second threader loop end defining a suture capture loop.

25. A knotless suture anchor comprising:
   an anchor body having an exterior surface, a proximal end, a distal end, a longitudinal axis extending between the proximal and distal end, an interior longitudinal passageway extending at least partway from the proximal end toward the distal end, a proximal opening communicating with the longitudinal passageway nearer the proximal end, and a distal opening communicating with the longitudinal passageway nearer the distal end;
   a proximal member joined to the anchor body by a frangible connection, the proximal member having a sidewall defining a proximal member axial passage coaxial with the longitudinal passageway, the proximal member having an aperture through the sidewall adjacent to the frangible connection, the proximal member being operable to break away from the anchor body at the frangible connection causing the aperture to open distally.

26. The knotless suture anchor of example 25 further comprising an interference member mounted in the proximal member axial passage in coaxial sliding relationship.

27. The knotless suture anchor of example 25 wherein the anchor body has a plurality of distal openings.

28. The knotless suture anchor of example 27 wherein the plurality of distal openings comprises a single opening on a first side of the anchor body and a pair of openings on a second side of the anchor body opposite the first side.

29. The knotless suture anchor of example 27 wherein the plurality of distal openings comprises first and second openings through a sidewall of the anchor body nearer the distal end than the proximal end.

30. The knotless suture anchor of example 27 wherein at least two of the plurality of distal openings have suture material passing through them.

31. The knotless suture anchor of example 25 further comprising an interference member retainer having a retainer axial passage, the interference member retainer engaging the proximal member axial passage in axial sliding relationship, and an interference member engaging the retainer member axial passage in axial sliding relationship.

32. The knotless suture anchor of example 31 further comprising an inserter operable to engage the proximal member in axial force transmitting relationship in a first direction, the inserter having a pushrod mounted for axial translation within the inserter, the pushrod being operable to engage the interference member in axial force transmitting relationship in a second direction opposite the first direction and expel the interference member from the proximal member into the anchor body, the pushrod being further operable to engage the interference member retainer in axial force transmitting relationship to press the interference member retainer against the anchor body and separate the anchor body and proximal member at the frangible connection.

33. A knotless suture anchor comprising:
   an anchor body having an exterior surface, a proximal end, a distal end, a longitudinal axis extending between the proximal and distal end, an interior longitudinal passageway extending at least partway from the proximal end toward the distal end, a proximal opening communicating with the longitudinal passageway nearer the proximal end, and a plurality of distal openings communicating with the longitudinal passageway nearer the distal end, the plurality of distal openings comprising a single opening on a first side of the anchor body and a pair of openings on a second side of the anchor body opposite the first side; and
   an interference member receivable within the longitudinal passageway.

34. A knotless suture anchor comprising:
   an anchor body having an exterior surface, a proximal end, a distal end, a longitudinal axis extending between the proximal and distal end, an interior longitudinal passageway extending at least partway from the proximal end toward the distal end, a proximal opening communicating with the longitudinal passageway nearer the proximal end, and a first distal opening communicating with the longitudinal passageway nearer the distal end;
   a first suture extending through the longitudinal passageway with a proximal end exiting the proximal opening and a distal end exiting the first distal opening;

a suture keeper joined to the first suture proximal end, the suture keeper being operable to prevent the proximal end of the first suture from passing through the proximal opening.

35. The knotless suture anchor of example 34 wherein the proximal end of the first suture is tied to the suture keeper.

36. The knotless suture anchor of example 34 wherein the suture keeper comprises a planar member having a portion for receiving the anchor body and releasably retaining the anchor body on the planar member.

37. The knotless suture anchor of example 36 wherein the first suture is wrapped around the planar member.

38. The knotless suture anchor of example 37 further comprising a second suture strand and a second distal opening, the first suture strand exiting the first distal opening and the second suture strand exiting the second distal opening, the planar member defining a first recess for receiving the first suture strand wrapped around the planar member and a second recess for receiving the second suture strand wrapped around the planar member.

39. The knotless suture anchor of example 38 further comprising a frangible elongate tube having a proximal end and a distal end, wherein after exiting the distal openings of the anchor body, the first and second suture strands pass through the tube from the proximal end to the distal end.

40. The knotless suture anchor of example 39 further comprising a suture threader, the suture threader including a filament forming a loop portion and a grip portion joined to the loop portion, and further wherein the anchor body comprises a third distal opening, the loop portion extending through the longitudinal passageway from the third distal opening to the proximal opening with at least part of the loop portion extending out of the proximal opening and the grip portion extending out of the third distal opening.

41. A method of attaching a suture to a bone, comprising:
passing a portion of a suture through a bone so that a first portion of the suture extends from a first opening in the bone and a second portion of the suture extends from a second opening in the bone;
passing the second portion of the suture through a portion of a suture anchor body in a proximal to distal direction, the suture anchor body having a proximal end and a distal end;
passing the second portion of the suture alongside an outer surface of the suture anchor body in a distal to proximal direction; and
then inserting the suture anchor into the bone through one of the first and second openings, the distal end being inserted first through the opening.

42. The method of example 41 wherein the step of passing the second portion of the suture longitudinally through a portion of a suture anchor body in a proximal to distal direction comprises engaging the second portion of the suture with a first suture threader and pulling the suture threader through the anchor, the first suture threader being preloaded on the suture anchor.

43. The method of example 41 further comprising passing the first portion of the suture longitudinally through a portion of the suture anchor body in a distal to proximal direction.

44. The method of example 43 wherein the step of passing the first portion of the suture longitudinally through a portion of the suture anchor body in a distal to proximal direction comprises engaging the second portion of the suture with a second suture threader and pulling the suture threader through the anchor, the second suture threader being preloaded on the suture anchor.

45. The method of example 41 further comprising after inserting the suture anchor into a hole in the bone, advancing a locking member into the suture anchor to lock the suture to the anchor.

46. The method of example 44 further comprising before advancing the locking member, tensioning the suture.

47. The method of example 44 wherein a proximal member is joined to the proximal end of the anchor by a frangible connection, the method further comprising after advancing the locking member, separating the proximal member and anchor at the frangible connection.

48. The method of example 47 wherein the proximal member includes a hole through a sidewall adjacent the frangible portion and the suture extends through the hole, further wherein separating the proximal member and anchor transforms the hole into a distally opening slot and releases the suture distally from the slot.

49. A method of attaching a suture to a bone, comprising:
disengaging a first portion of a suture extending from a distal end of a suture anchor from a suture keeper, a second portion of the suture extending from a proximal end of the suture anchor being joined to the suture keeper;
then passing the first suture portion through a patient's body tissue;
then inserting the suture anchor body into a hole in a bone;
then separating the suture keeper from the second portion of the suture.

50. The method of example 49 wherein the second portion includes at least first and second strands of suture, the first strand being joined to a first portion of the suture keeper and the second strand being joined to a second portion of the suture keeper, the method further comprising independently tensioning the first and second strands.

51. The method of example 49 further comprising sliding the suture anchor over the first portion of suture away from the suture keeper while the second portion remains joined to the suture keeper.

52. A method of attaching soft tissue to bone, comprising:
passing a first portion of a suture through a bone;
passing the first portion through a soft tissue;
passing the first portion outside of a patient's body;
tying a knot in the first portion; and
pulling a second portion of the suture joined to the first portion to move the knot into the patient to a position adjacent to the soft tissue; and
securing the suture to the bone.

53. A method of attaching soft tissue to bone, comprising:
passing a tube through a portal in a patient's skin, the tube having a suture passing through it;
passing the suture through a soft tissue;
splitting the tube to free the suture from the tube; and
anchoring the suture to a bone.

54. A method of attaching a suture to a bone, comprising:
providing a suture anchor having a proximal end, a distal end, a longitudinal passage extending within the suture anchor in a proximal to distal direction, a first opening communicating with the longitudinal passage nearer the proximal end than the distal end, a second opening through the sidewall of the suture anchor nearer the distal end than the proximal end, and a third opening through the sidewall of the suture anchor nearer the distal end than the proximal end, a first suture threader extending within the longitudinal passage between the first and third openings, the first suture threader extending through the first opening to a grip portion outside of the longitudinal passage, the first suture threader extending through the third opening to a suture engaging portion outside of the longitudinal passage, a second suture threader extending within the longitudinal passage between the first and second openings, the second suture threader extending through the first opening to a suture engaging portion outside of the longitudinal passage, the second suture threader extending through the second opening to a grip portion outside of the longitudinal passage, passing a portion of a suture through a bone so that a first portion of the suture extends from a first opening in the bone and a second portion of the suture extends from a second opening in the bone;

engaging the first portion of the suture with the first suture passer;

pulling on the grip portion of the first suture passer to pass the first portion of the suture through the longitudinal passage in a distal to proximal direction;

engaging the second portion of the suture with the second suture passer;

pulling on the grip portion of the second suture passer to pass the second portion of the suture through the longitudinal passage in a proximal to distal direction; and then inserting the suture anchor into the bone through one of the first and second openings, the distal end being inserted first through the opening.

55. The method of example 54 further comprising:
passing the second portion of the suture through soft tissue;
tying a knot in the second portion of the suture outside of a patient's body; and
pulling on the first portion of the suture to move the knot nearer to the soft tissue.

56. The method of example 54 further comprising:
passing the first portion of the suture through a tube;
placing the tube and first portion of the suture through a portal in the patient's body;
splitting the tube to free the suture laterally from the tube.

57. The method of example 54 further comprising passing the second portion alongside an outer surface of the anchor in a distal to proximal direction.

58. The method of example 54 further comprising advancing a locking member in the longitudinal passage to secure the suture within the longitudinal passage.

59. The method of example 58 wherein a proximal member is joined to the proximal end of the anchor by a frangible connection, the proximal member housing the locking member, the step of advancing the locking member comprising pressing the locking member from the proximal member into the longitudinal passage, the method further comprising after advancing the locking member, separating the proximal member and anchor at the frangible connection.

60. The method of example 59 wherein advancing the locking member comprises actuating an inserter to press the locking member in a first direction while applying a counterforce to the proximal member in a second direction opposite the first direction, and wherein separating the proximal member and anchor comprises further actuating the inserter to break the frangible connection.

What is claimed is:

1. A method of attaching a suture to a bone, comprising:
passing a portion of a suture through a bone so that a first portion of the suture extends from a first opening in the bone and a second portion of the suture extends from a second opening in the bone;
passing the second portion of the suture through a portion of a suture anchor body in a proximal to distal direction, the suture anchor body having a proximal end and a distal end;
passing the second portion of the suture alongside an outer surface of the suture anchor body in a distal to proximal direction; and
then inserting the suture anchor into the bone through one of the first and second openings, the distal end being inserted first through the opening.

2. The method of claim 1 wherein the step of passing the second portion of the suture longitudinally through a portion of a suture anchor body in a proximal to distal direction comprises engaging the second portion of the suture with a first suture threader and pulling the suture threader through the anchor, the first suture threader being preloaded on the suture anchor.

3. The method of claim 1 further comprising passing the first portion of the suture longitudinally through a portion of the suture anchor body in a distal to proximal direction.

4. The method of claim 3 wherein the step of passing the first portion of the suture longitudinally through a portion of the suture anchor body in a distal to proximal direction comprises engaging the second portion of the suture with a second suture threader and pulling the suture threader through the anchor, the second suture threader being preloaded on the suture anchor.

5. The method of claim 1 further comprising after inserting the suture anchor into a hole in the bone, advancing a locking member into the suture anchor to lock the suture to the anchor.

6. The method of claim 4 further comprising before advancing the locking member, tensioning the suture.

7. The method of claim 4 wherein a proximal member is joined to the proximal end of the anchor by a frangible connection, the method further comprising after advancing the locking member, separating the proximal member and anchor at the frangible connection.

8. The method of claim 7 wherein the proximal member includes a hole through a sidewall adjacent the frangible portion and the suture extends through the hole, further wherein separating the proximal member and anchor transforms the hole into a distally opening slot and releases the suture distally from the slot.

9. A method of attaching a suture to a bone, comprising:
disengaging a first portion of a suture extending from a distal end of a suture anchor from a suture keeper, a second portion of the suture extending from a proximal end of the suture anchor being joined to the suture keeper;
then passing the first suture portion through a patient's body tissue;
then inserting the suture anchor body into a hole in a bone; and
then separating the suture keeper from the second portion of the suture.

10. The method of claim 9 wherein the second portion includes at least first and second strands of suture, the first strand being joined to a first portion of the suture keeper and the second strand being joined to a second portion of the suture keeper, the method further comprising independently tensioning the first and second strands.

11. The method of claim 9 further comprising sliding the suture anchor over the first portion of suture away from the suture keeper while the second portion remains joined to the suture keeper.

12. A method of attaching soft tissue to bone, comprising:
passing a tube through a portal in a patient's skin, the tube having a suture passing through it;
passing the suture through a soft tissue;
splitting the tube to free the suture from the tube; and
anchoring the suture to a bone.

13. A method of attaching a suture to a bone, comprising:
providing a suture anchor having a proximal end, a distal end, a longitudinal passage extending within the suture anchor in a proximal to distal direction, a first opening communicating with the longitudinal passage nearer the proximal end than the distal end, a second opening through the sidewall of the suture anchor nearer the distal end than the proximal end, and a third opening through the sidewall of the suture anchor nearer the distal end than the proximal end, a first suture threader extending within the longitudinal passage between the first and third openings, the first suture threader extending through the first opening to a grip portion outside of the longitudinal passage, the first suture threader extending through the third opening to a suture engaging portion outside of the longitudinal passage, a second suture threader extending within the longitudinal passage between the first and second openings, the second suture threader extending through the first opening to a suture engaging portion outside of the longitudinal passage, the second suture threader extending through the second opening to a grip portion outside of the longitudinal passage;
passing a portion of a suture through a bone so that a first portion of the suture extends from a first opening in the bone and a second portion of the suture extends from a second opening in the bone;
engaging the first portion of the suture with the first suture threader;
pulling on the grip portion of the first suture threader to pass the first portion of the suture through the longitudinal passage in a distal to proximal direction;
engaging the second portion of the suture with the second suture threader;
pulling on the grip portion of the second suture threader to pass the second portion of the suture through the longitudinal passage in a proximal to distal direction; and
then inserting the suture anchor into the bone through one of the first and second openings, the distal end being inserted first through the opening.

14. The method of claim 13 further comprising:
passing the second portion of the suture through soft tissue;
tying a knot in the second portion of the suture outside of a patient's body; and
pulling on the first portion of the suture to move the knot nearer to the soft tissue.

15. The method of claim 13 further comprising:
passing the first portion of the suture through a tube;
placing the tube and first portion of the suture through a portal in the patient's body;
splitting the tube to free the suture laterally from the tube.

16. The method of claim 13 further comprising passing the second portion alongside an outer surface of the anchor in a distal to proximal direction.

17. The method of claim 13 further comprising advancing a locking member in the longitudinal passage to secure the suture within the longitudinal passage.

18. The method of claim 17 wherein a proximal member is joined to the proximal end of the anchor by a frangible connection, the proximal member housing the locking member, the step of advancing the locking member comprising pressing the locking member from the proximal member into the longitudinal passage, the method further comprising after advancing the locking member, separating the proximal member and anchor at the frangible connection.

19. The method of claim 18 wherein advancing the locking member comprises actuating an inserter to press the locking member in a first direction while applying a counterforce to the proximal member in a second direction opposite the first direction, and wherein separating the proximal member and anchor comprises further actuating the inserter to break the frangible connection.

* * * * *